US012569496B2

(12) United States Patent
Franovic et al.

(10) Patent No.: US 12,569,496 B2
(45) **Date of Patent: *Mar. 10, 2026**

(54) TREATMENT OF CANCER WITH A RAF INHIBITOR

(71) Applicant: PIERRE FABRE MEDICAMENT, Lavaur (FR)

(72) Inventors: Aleksandra Franovic, Del Mar, CA (US); Eric Martin, Del Mar, CA (US); Nichol L. G. Miller, Poway, CA (US); Eric Murphy, San Marcos, CA (US); Richard Thomas Williams, Newbury Park, CA (US); Ken Kobayashi, San Diego, CA (US)

(73) Assignee: PIERRE FABRE MÉDICAMENT, Lavaur (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/424,274

(22) Filed: Jan. 26, 2024

(65) Prior Publication Data

US 2024/0325403 A1 Oct. 3, 2024

Related U.S. Application Data

(63) Continuation of application No. 18/296,726, filed on Apr. 6, 2023, now Pat. No. 11,918,587, which is a continuation of application No. PCT/US2022/025875, filed on Apr. 22, 2022.

(60) Provisional application No. 63/178,922, filed on Apr. 23, 2021.

(51) Int. Cl.
*A61K 31/5377* (2006.01)
*A61K 45/06* (2006.01)
*A61P 35/00* (2006.01)

(52) U.S. Cl.
CPC .......... *A61K 31/5377* (2013.01); *A61K 45/06* (2013.01); *A61P 35/00* (2018.01)

(58) Field of Classification Search
CPC ............ A61K 31/4439; A61K 31/5377; A61K 45/06; A61P 35/00
See application file for complete search history.

(56) References Cited

U.S. PATENT DOCUMENTS

| | | | | |
|---|---|---|---|---|
| 5,846,514 | A | 12/1998 | Foster et al. | |
| 6,334,997 | B1 | 1/2002 | Foster et al. | |
| 10,927,111 | B2 | 2/2021 | Kaldaor et al. | |
| 11,098,031 | B1 * | 8/2021 | Kaldor | A61K 31/444 |
| 11,377,431 | B2 | 7/2022 | Kaldor et al. | |
| 11,407,737 | B2 * | 8/2022 | Kaldor | C07D 417/14 |
| 11,667,634 | B2 | 6/2023 | Kaldor et al. | |
| 11,746,095 | B2 | 9/2023 | Kaldor et al. | |
| 11,918,587 | B2 * | 3/2024 | Franovic | A61K 45/06 |
| 12,312,336 | B2 * | 5/2025 | Kaldor | C07D 403/12 |
| 2004/0157827 | A1 | 8/2004 | Pevarello et al. | |
| 2005/0256174 | A1 | 11/2005 | Wood et al. | |
| 2007/0054916 | A1 | 3/2007 | Patel et al. | |
| 2007/0244120 | A1 | 10/2007 | Dumas et al. | |
| 2008/0114006 | A1 | 5/2008 | Flynn et al. | |
| 2009/0036419 | A1 | 2/2009 | Chen et al. | |
| 2009/0054436 | A1 | 2/2009 | Borzilleri et al. | |
| 2011/0183997 | A1 | 7/2011 | Chianelli et al. | |
| 2012/0040951 | A1 | 2/2012 | Chuaqui et al. | |
| 2014/0275003 | A1 | 9/2014 | Barsanti et al. | |
| 2015/0119392 | A1 | 4/2015 | Flynn et al. | |
| 2016/0075727 | A1 | 3/2016 | Burger et al. | |
| 2017/0260207 | A1 | 9/2017 | Aversa et al. | |
| 2019/0175606 | A1 | 6/2019 | Aversa et al. | |
| 2020/0347052 | A1 | 11/2020 | Kaldor et al. | |
| 2021/0300904 | A1 | 9/2021 | Kaldor et al. | |
| 2022/0340543 | A1 | 10/2022 | Kaldor et al. | |
| 2023/0081390 | A1 | 3/2023 | Kaldaor et al. | |

FOREIGN PATENT DOCUMENTS

| | | | | |
|---|---|---|---|---|
| EP | 2112150 B1 | 10/2013 | | |
| WO | WO-03068229 A1 | 8/2003 | | |
| WO | WO-2006071940 A2 | 7/2006 | | |
| WO | WO-2008034008 A2 | 3/2008 | | |
| WO | WO-2013184119 A1 | 12/2013 | | |
| WO | WO-2014151616 A1 | 9/2014 | | |
| WO | WO-2016038581 A1 | 3/2016 | | |
| WO | WO-2016038582 A1 | 3/2016 | | |
| WO | WO-2020168172 A1 | 8/2020 | | |
| WO | WO-2020198058 A1 | 10/2020 | | |
| WO | WO-2020227020 A1 | 11/2020 | | |
| WO | WO-2021076602 A1 | 4/2021 | | |
| WO | WO-2021081375 A1 * | 4/2021 | A61K 31/4439 | |
| WO | WO-2022060996 A1 | 3/2022 | | |
| WO | WO-2022081469 A1 | 4/2022 | | |

(Continued)

OTHER PUBLICATIONS

Dummer (Lancet Oncology vol. 19 pp. 603-615. Published 2018) (Year: 2018).*
Henry (J. Med. Chem vol. 58 pp. 4165-4179 published 2015). (Year: 2015).*
Karoulia (Nature Review Cancer vol. 17 pp. 676-691 Published 2017) (Year: 2017).*
Anastassiadis et al. Comprehensive assay of kinase catalytic activity reveals features of kinase inhibitor selectivity. Nat Biotechnol. 29(11):1039-45 (2011).
Berge et al., Pharmaceutical Salts. Journal of Pharmaceutical Sciences 66(1):1-19 (Jan. 1977).
CAS Chemical Structure Search #3191415 Updated (Apr. 2020).
CAS Chemical Structure Search dated Apr. 24, 2019.
CAS Search dated Apr. 26, 2023.

(Continued)

*Primary Examiner* — George W Kosturko
(74) *Attorney, Agent, or Firm* — Birch, Stewart, Kolasch & Birch, LLP

(57) ABSTRACT

Provided herein are compositions and methods for the treatment of a cancer. Said compositions comprise a RAF inhibitor. Some embodiments comprise combination therapy featuring the RAF inhibitor with at least one oncology therapeutic agent.

31 Claims, 12 Drawing Sheets

(56) References Cited

FOREIGN PATENT DOCUMENTS

| | | | |
|---|---|---|---|
| WO | WO-2022226221 | A1 | 10/2022 |
| WO | WO-2022226261 | A1 | 10/2022 |

OTHER PUBLICATIONS

Chapman et al. Improved survival with vemurafenib in melanoma with BRAF V600E mutation. New England Journal of Medicine 364(26):2507-2516 (2011).
Chemical Structure Search report data Feb. 27, 2019.
Davies et al. Mutations of the BRAF Gene in Human Cancer. Nature 417:949-954 (2002).
Evans. Synthesis of Radiolabelled Compounds. Journal of Radioanalytical Chemistry 64(1-2):9-32 (1981).
Hauschild et al. Dabrafenib in BRAF-mutated Metastatic Melanoma: A Multicentre, Open-Label, Phase 3 Randomised Controlled Trial. Lancet 380(9839):358-65 (2012).
Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).
Kabalka et al., The synthesis of radiolabeled compounds via organometallic intermediates. Tetrahedron 45(21):6601-6621 (1989).
Kania et al. The Discovery of Exarafenib (KIN-2787), a Solution to the Challenges of Pan-RAF kinase Inhibition. PowerPoint presentation at Winter Conference on Medicinal & Bioorganic Chemistry (Jan. 2023).
Kinnate Biopharma. RAF Clinico-Genomic Landscape Study PowerPoint. (Nov. 2021).
Lv et al. Design, synthesis and biological evaluation of novel 4-alkynylquinoline derivatives as PI3K/mTOR dual inhibitors. Eur J Med Chem 99:36-50 (2015).
Manabe. Antitumor activity of KIN-2787, a next-generation pan-RAF inhibitor, in preclinical models of human BRAF-alteration driven non-small cell lung cancer (NSCLC). Presentation from IASLC 2022 Targeted Therapies of Lung Cancer Meeting. Feb. 22-26, 2022.
McKean et al. Design and rationale of a first in human (FIH) phase 1/1b study evaluating KIN-2787, a potent and highly selective pan-RAF inhibitor, in adult patients with BRAF- and NRAS-mutation positive solid tumors. American Association for Cancer Research Annual Meeting. Poster #CT248 (2022).
Miller et al. Antitumor activity of KIN-2787, a next-generation pan-RAF inhibitor, in preclinical models of human RAF/RAS mutant melanoma. American Association for Cancer Research Poster #2674 (2022).
Nishiguchi et al. Design and Discovery of N-(2-Methyl-5'-morpholino-6'-((tetrahydro-2H-pyran-4-yl)oxy)-[3,3'-bipyridin]-5-yl)-3-(trifluoromethyl)benzamide (RAF709): A Potent, Selective, and Efficacious RAF Inhibitor Targeting RAS Mutant Cancers. J Med Chem 60(12):4869-4881 (2017).
Owsley et al. Prevalence of class I-III BRAF mutations among 114,662 cancer patients in a large genomic database. Exp Biol Med (Maywood) 246(1):31-39 (2021).
PCT/US2020/024009 International Invitation to Pay Additional Fees dated Jun. 2, 2020.
PCT/US2020/024009 International Search Report and Written Opinion dated Jul. 28, 2020.
PCT/US2020/030786 International Invitation to Pay Additional Fees dated Jul. 14, 2020.
PCT/US2020/030786 International Search Report and Written Opinion dated Sep. 14, 2020.
PCT/US2020/057132 International Invitation to Pay Additional Fees dated Dec. 8, 2020.
PCT/US2020/057132 International Search Report and Written Opinion dated Feb. 9, 2021.
PCT/US2021/050690 International Search Report and Written Opinion dated Dec. 27, 2021.
PCT/US2021/054403 International Search Report and Written Opinion dated Dec. 28, 2021.
PCT/US2022/025815 International Search Report and Written Opinion dated Jul. 28, 2022.
PCT/US2022/025875 International Search Report and Written Opinion dated Jul. 25, 2022.
Ramurthy et al., Design and Discovery of N-(3-(2-(2-Hydroxyethoxy)-6-morpholinopyridin-4-yl)-4-methylphenyl)-2-(trifluoromethyl)isonicotinamide, a Selective, Efficacious, and Well-Tolerated RAF Inhibitor Targeting RAS Mutant Cancers: The Path to the Clinic. Journal of Medicinal Chemistry 63(5):2013-2027 (2020).
Reg/Caplus and Marpat. Science IP Report dated Sep. 17, 2020.
Rosse. Pyridyl Isonicotinamide Inhibitors of RAF Kinase. ACS Med. Chem. Lett. 7:1022-1023 (2016).
Science IP Report dated Jul. 13, 2020 (873 pgs).
Severson et al. Occurrence of BRAF class II and III alterations is common across solid tumors and is associated with inferior clinical outcomes in NSCLC and melanoma. American Association for Cancer Research Poster #4122 (2022).
Severson et al. Real-World Clinical Genomic Analysis of Patients with BRAF Mutated Cancers Identifies BRAF Class II and III as a Population of Unmet Medical Need. ESMO Targeted Anticancer Therapies Congress 2022. Poster 40P.
Spira et al. A Phase 1 Clinical Trial Evaluating Monotherapy With Exarafenib (KIN-2787), a Highly Selective Pan-RAF Inhibitor, in BRAF-Altered Solid Tumors and NRAS-Mutant Melanoma. PowerPoint Presentation American Association for Cancer Research Annual Meeting Apr. 14-19, 2023.
Subbiah et al. Pan-Cancer Efficacy of Vemurafenib in BRAF V600-Mutant Non-Melanoma Cancers. Cancer Discov 10(5):657-663 (2020).
U.S. Appl. No. 17/167,599 Office Action dated Oct. 31, 2022.
U.S. Appl. No. 17/738,327 Office Action dated Apr. 18, 2023.
U.S. Appl. No. 18/296,726 Office Action dated Jul. 18, 2023.
Wang et al. Exarafenib (KIN-2787) is a potent, selective pan-RAF inhibitor with activity in preclinical models of BRAF Class II/III mutant and NRAS mutant melanoma. American Association for Cancer Research Annual Meeting Poster #4927 (2023).
Yaeger et al. Targeting Alterations in the RAF-MEK Pathway. Cancer Discov 9(3):329-341 (2019).

* cited by examiner

TREATMENT OF CANCER WITH A RAF INHIBITOR

CROSS-REFERENCE TO RELATED APPLICATION

This application is a continuation of U.S. patent application Ser. No. 18/296,726, filed on Apr. 6, 2023; which is a continuation of International Patent Application No. PCT/US2022/025875, filed on Apr. 22, 2022; and claims benefit of U.S. Patent Application No. 63/178,922, filed on Apr. 23, 2021, all of which are hereby incorporated by reference in their entirety.

BACKGROUND OF THE INVENTION

RAF kinase functions in the Ras-Raf-MEK-ERK mitogen activated protein kinase (MAPK) pathway (also known as MAPK/ERK pathway) by phosphorylating and activating MEK and ultimately MAPK-dependent activation of transcriptional programs drives cell proliferation and survival. Deregulation of MAPK activity occurs frequently in tumors. Accordingly, therapies that target RAF kinase activity are desired for use in the treatment of cancer and other disorders characterized by aberrant MAPK/ERK pathway signaling.

BRIEF SUMMARY

One embodiment provides a method of treating a cancer in a patient in need thereof, comprising administering to the patient (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof.

One embodiment provides a method of treating a cancer in a patient in need thereof, comprising administering to the patient a pharmaceutical composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, and at least one pharmaceutically acceptable excipient.

One embodiment provides a method of treating a cancer in a patient in need thereof, comprising administering to the patient:

(a) a composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof; and (b) at least one oncology therapeutic selected from a MEK inhibitor, an immune checkpoint inhibitor, a CDK inhibitor, an EGFR kinase inhibitor, an EGFR antibody, an EGFR PROTAC therapeutic, a FGFR inhibitor, a SOS1 inhibitor, a SHP2 inhibitor, a KRAS inhibitor, a taxane, a topoisomerase inhibitor, an ERK inhibitor, a platinum-based chemotherapy, folinic acid, 5-fluorouracil, or an anti-VEGF therapeutic.

INCORPORATION BY REFERENCE

Figure 1A:
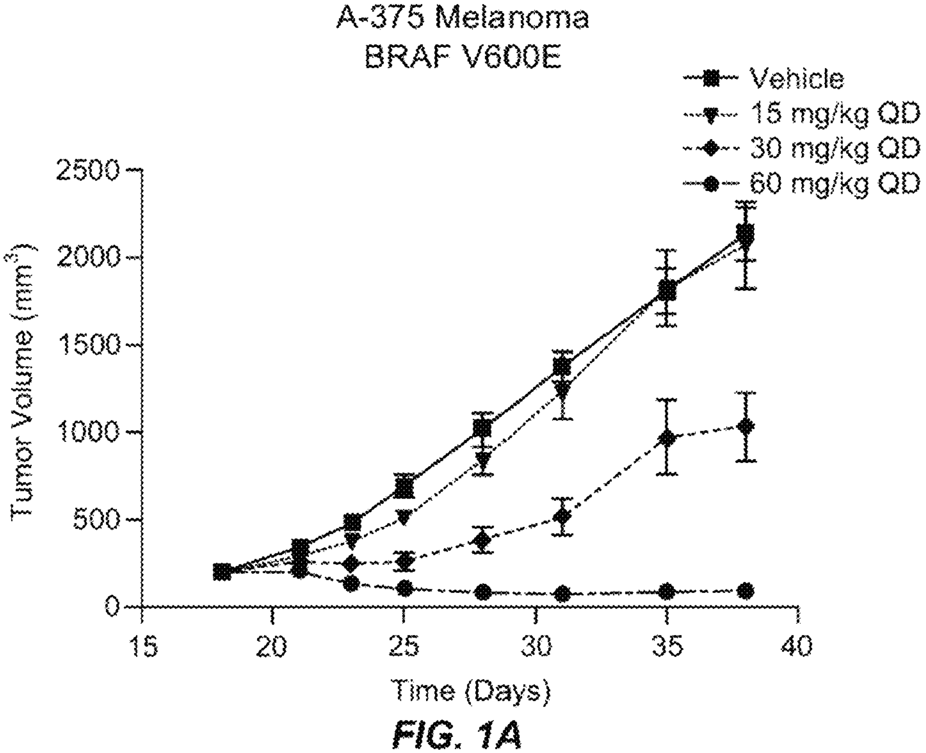
FIGS. 1A-1C illustrates A-375 (Class I BRAF mutant melanoma) xenograft tumor volumes (FIG. 1A), mouse body weight (FIG. 1B), and percent change in xenograft tumor volumes at end of study relative to baseline (FIG. 1C) following treatment with Compound 1.

All publications, patents, and patent applications mentioned in this specification are hereby incorporated by reference for the specific purposes identified herein.

DETAILED DESCRIPTION

Certain Terminology

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and sub-combinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below.

"Pharmaceutically acceptable salt" includes both acid and base addition salts. A pharmaceutically acceptable salt of the heterocyclic RAF inhibitor described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science,* 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. The compounds provided herein optionally exist in either unsolvated as well as solvated forms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made. The term "treating", as used herein, unless otherwise indicated, means reversing, alleviating, inhibiting the progress of, or preventing the disorder or condition to which such term applies, or one or more symptoms of such disorder or condition. In some embodiments, the tern "treating" includes slowing or delaying the progression of the disease or disorder to which the term is applied. Additionally, in some embodiments, the term "treating" is applied to one or more of the complications resulting from the disease or disorder to which the term is applied. The term "treatment", as used herein, unless otherwise indicated, refers to the act of treating as "treating" is defined immediately above.

The term "tumor," or "cancer" as used herein, and unless otherwise specified, refers to a neoplastic cell growth, and includes pre-cancerous and cancerous cells and tissues. Tumors usually present as a lesion or lump. As used herein, "treating" a tumor means that one or more symptoms of the disease, such as the tumor itself, vascularization of the tumor, or other parameters by which the disease is characterized, are reduced, ameliorated, inhibited, placed in a state of remission, or maintained in a state of remission. "Treating" a tumor also means that one or more hallmarks of the tumor may be eliminated, reduced or prevented by the treatment. Non-limiting examples of such hallmarks include uncontrolled degradation of the basement membrane and proximal extracellular matrix, migration, division, and organization of the endothelial cells into new functioning capillaries, and the persistence of such functioning capillaries.

The term "refractory" or "refractory to therapy" indicates that the patients have never responded to therapy.

The term “relapsed” or “relapsed after therapy” indicates that patients, after initially responding to prior therapy, have progressive disease due to acquired resistance and/or intolerance.

The term “resistance to therapy” or “acquired resistance to therapy” indicates the patients, after initially responding to prior therapy, have progressive disease due to clinical or molecular resistance to the therapy. The acquired resistance can result from emergence of resistant mutations in the molecular target of the therapy, or in the development of physiological functions such as efflux pumps.

The phrase “therapeutically effective amount”, as used herein, refers to that amount of drug or pharmaceutical agent that will elicit the biological or medical response of a tissue, system, animal, or human that is being sought by a researcher, veterinarian, medical doctor or other.

Other aspects, advantages, and features of the invention will become apparent from the detailed description below.

RAF Family Kinase

RAF family kinases (ARAF, BRAF, and RAF1) act downstream of receptor tyrosine kinases (RTKs) to regulate key cellular functions via modulation of the MAPK signaling pathway. In normal cells, external ligand stimulation of RTKs activates RAS GTPases that promote RAF dimer formation, protomer transactivation, and ultimately MAPK-dependent activation of transcriptional programs that drive cell proliferation and survival (Zaman et al 2019). Mutational activation of the RTK-RAS-RAF-MAPK pathway is frequently observed in human cancers and represents a well-established target for therapeutic intervention (Roberts & Der 2007, Imperial et al 2017).

Oncogenic BRAF alterations occur in approximately 4-8% of all human cancers and can be functionally categorized into three classes based on their unique structural and signaling properties (Davies, 2002; Owsley, 2020). Class I BRAF V600 mutations result in active BRAF monomers that signal independent of RAS recruitment and RAF dimerization/protomer transactivation (Yaeger & Corcoran, 2019). Class II BRAF mutations lead to RAS-independent BRAF dimerization and protomer transactivation. Class III BRAF mutations impair BRAF kinase activity but promote its association with RAS. In this case, amplified MAPK signaling remains dependent on upstream RAS activation and heterodimerization with wild-type RAF (ARAF or RAF1). In contrast to the constitutively active Class I and II BRAF mutations that rarely co-occur with other MAPK pathway alterations, Class III BRAF alterations are often observed in association with aberrant RAS activation, via RTK dysregulation, RAS mutations, or NF1 loss-of-function (Yeager & Corcoran, 2019).

The first-generation BRAF inhibitors (e.g., vemurafenib, dabrafenib) target Class I mutations and have conferred significant clinical benefit to patients with BRAF V600 mutation-driven metastatic melanoma (~50% objective response rate; 5-6 month median progression-free survival) as monotherapies, as well as other cancer types as part of combination therapy regimens (Chapman, 2011; Hauschild, 2012; Subbiah, 2020). The currently approved BRAF inhibitors have not, however, proven to be effective in patients harboring Class II and III BRAF mutations which account for a significant proportion of BRAF mutations (e.g., 65% in NSCLC and 21% in melanoma patients; Owsley, 2021). While RAF inhibitors designed to be effective in all classes of BRAF mutations are desirable, Class II and III BRAF altered tumors are resistant to current FDA approved therapies and represent patient populations with unmet clinical needs.

Heterocyclic RAF Inhibitor

The heterocyclic RAF inhibitor described herein refers to Compound 1 having the structure below, and the chemical name (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide.

Compound 1

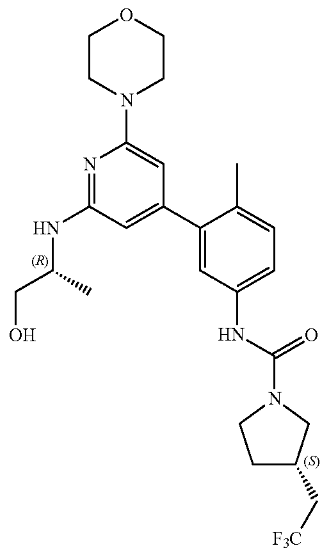

Compound 1 is a reversible small molecule RAF inhibitor. Throughout this disclosure when reference is made to a heterocyclic RAF inhibitor, or pharmaceutically acceptable salts or solvates thereof, the reference is to Compound 1, and pharmaceutically acceptable salts or solvates thereof.

Cancer and Methods of Treatment

In one embodiment is a method for inhibiting RAF enzyme comprising contacting the enzyme with Compound 1, or pharmaceutically acceptable salts or solvates thereof, as disclosed herein. In certain aspects, disclosed herein is a method of treating a cancer in an individual in need thereof, comprising administering an effective amount of a heterocyclic RAF inhibitor described herein to the individual. In certain aspects, disclosed herein is a heterocyclic RAF inhibitor described herein for use in treating a cancer. In certain aspects, disclosed herein is a heterocyclic RAF inhibitor described herein for use in preparation of a medicament for treating a cancer.

One embodiment provides a method of treating a cancer in a patient in need thereof, comprising administering to the patient (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof. Another embodiment provides the method, wherein the cancer is characterized as having an oncogenic BRAF alteration. Another embodiment provides the method, wherein the oncogenic BRAF alteration is a Class I BRAF mutation. Another embodiment provides the method, wherein the oncogenic BRAF alteration is a Class II BRAF mutation. Another embodiment provides the method, wherein the oncogenic BRAF alteration is a Class III BRAF mutation. Another embodiment provides the method, wherein the oncogenic BRAF alteration is a BRAF V600 mutation. Another embodiment provides the method, wherein the BRAF V600 mutation is a V600E or V600K mutation. Another embodiment provides the method, wherein the cancer is characterized as having a wild type BRAF. Another embodiment provides the method, wherein the cancer is a solid tumor. Another embodiment provides the method, wherein the cancer is an NRAS mutant tumor. Another embodiment provides the method, wherein the cancer is selected from melanoma, pancreatic cancer, pancreatic adenocarcinoma, ovarian cancer, colorectal cancer, glioma, Langerhans cell histiocytosis, leukemia, hairy cell leukemia, thyroid cancer, anaplastic thyroid cancer, papillary thyroid carcinoma, follicular thyroid carcinoma, or medullary thyroid carcinoma. Another embodiment provides the method, wherein the cancer is selected from small cell lung cancer, non-small cell lung cancer, prostate cancer, gastric cancer, and esophageal cancer. Another embodiment provides the method, wherein the cancer is melanoma. Another embodiment provides the method, wherein the cancer is NRAS mutant melanoma. Another embodiment provides the method, wherein the cancer is pancreatic cancer. Another embodiment provides the method, wherein the cancer is pancreatic adenocarcinoma. Another embodiment provides the method, wherein the cancer is ovarian cancer. Another embodiment provides the method, wherein the cancer is colorectal cancer. Another embodiment provides the method, wherein the cancer is glioma. Another embodiment provides the method, wherein the cancer is Langerhans cell histiocytosis. Another embodiment provides the method, wherein the cancer is leukemia. Another embodiment provides the method, wherein the cancer is hairy cell leukemia. Another embodiment provides the method, wherein the cancer is thyroid cancer. Another embodiment provides the method, wherein the cancer is anaplastic thyroid cancer. Another embodiment provides the method, wherein the cancer is papillary thyroid carcinoma. Another embodiment provides the method, wherein the cancer is follicular thyroid carcinoma. Another embodiment provides the method, wherein the cancer is medullary thyroid carcinoma. Another embodiment provides the method, wherein the cancer is small cell lung cancer. Another embodiment provides the method, wherein the cancer is non-small cell lung cancer. Another embodiment provides the method, wherein the cancer is NRAS mutant non-small cell lung cancer. Another embodiment provides the method, wherein the cancer is NRAS mutant lung cancer. Another embodiment provides the method, wherein the cancer is prostate cancer. Another embodiment provides the method, wherein the cancer is gastric cancer. Another embodiment provides the method, wherein the cancer is cholangiocarcinoma. Another embodiment provides the method, wherein the cancer is esophageal cancer. Another embodiment provides the method, wherein the cancer is metastatic. Another embodiment provides the method, wherein the method is adjuvant therapy following surgical resection. Another embodiment provides the method, wherein the patient has relapsed after prior therapy. Another embodiment provides the method, wherein the patient has acquired resistance to prior therapy. Another embodiment provides the method, wherein the patient is refractory to therapy. Another embodiment provides the method, wherein the (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, is administered orally. Another embodiment provides the method, wherein the oral administration occurs every other day, once per day, twice per day, or three times per day.

One embodiment provides a method of treating a cancer in a patient in need thereof, comprising administering to the patient a pharmaceutical composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, and at least one pharmaceutically acceptable excipient. Another embodiment provides the method, wherein the cancer is characterized as having an oncogenic BRAF alteration. Another embodiment provides the method, wherein the oncogenic BRAF alteration is a Class I BRAF mutation. Another embodiment provides the method, wherein the oncogenic BRAF alteration is a Class II BRAF mutation. Another embodiment provides the method, wherein the oncogenic BRAF alteration is a Class III BRAF mutation. Another embodiment provides the method, wherein the oncogenic BRAF alteration is a BRAF V600 mutation. Another embodiment provides the method, wherein the BRAF V600 mutation is a V600E or V600K mutation. Another embodiment provides the method, wherein the cancer is characterized as having a wild type BRAF. Another embodiment provides the method, wherein the cancer is a solid tumor. Another embodiment provides the method, wherein the cancer is an NRAS mutant tumor. Another embodiment provides the method, wherein the cancer is selected from melanoma, pancreatic cancer, pancreatic adenocarcinoma, ovarian cancer, colorectal cancer, glioma, Langerhans cell histiocytosis, leukemia, hairy cell leukemia, thyroid cancer, anaplastic thyroid cancer, papillary thyroid carcinoma, follicular thyroid carcinoma, or medullary thyroid carcinoma. Another embodiment provides the method, wherein the cancer is selected from small cell lung cancer, non-small cell lung cancer, prostate cancer, gastric cancer, and esophageal cancer. Another embodiment provides the method, wherein the cancer is selected from melanoma. Another embodiment provides the method, wherein the cancer is NRAS mutant melanoma. Another embodiment provides the method, wherein the cancer is pancreatic cancer. Another embodiment provides the method, wherein the cancer is pancreatic adenocarcinoma. Another embodiment provides the method, wherein the cancer is ovarian cancer. Another embodiment provides the method, wherein the cancer is colorectal cancer. Another embodiment provides the method, wherein the cancer is glioma. Another embodiment provides the method, wherein the cancer is Langerhans cell histiocytosis. Another embodiment provides the method, wherein the cancer is leukemia. Another embodiment provides the method, wherein the cancer is hairy cell leukemia. Another embodiment provides the method, wherein the cancer is thyroid cancer. Another embodiment provides the method, wherein the cancer is anaplastic thyroid cancer. Another embodiment provides the method, wherein the cancer is papillary thyroid carcinoma. Another embodiment provides the method, wherein the cancer is follicular thyroid carcinoma. Another embodiment provides the method, wherein the cancer is medullary thyroid carcinoma. Another embodiment provides the method, wherein the cancer is small cell lung cancer. Another embodiment provides the method, wherein the cancer is non-small cell lung cancer. Another embodiment provides the method, wherein the cancer is NRAS mutant non-small cell lung cancer. Another embodiment provides the method, wherein the cancer is NRAS mutant lung cancer. Another embodiment provides the method, wherein the cancer is prostate cancer. Another embodiment provides the method, wherein the cancer is gastric cancer. Another embodiment provides the method, wherein the cancer is cholangiocarcinoma. Another embodiment provides the method, wherein the cancer is esophageal cancer. Another embodiment provides the method, wherein the cancer is metastatic. Another embodiment provides the method, wherein the method is adjuvant therapy following surgical resection. Another embodiment provides the method, wherein the patient has relapsed after prior therapy. Another embodiment provides the method, wherein the patient has acquired resistance to prior therapy. Another embodiment provides the method, wherein the patient is refractory to therapy. Another embodiment provides the method, wherein the (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, is administered orally. Another embodiment provides the method, wherein the oral administration occurs every other day, once per day, twice per day, or three times per day.

One embodiment provides a method of treating a cancer in a patient in need thereof, comprising administering to the patient:

(a) a composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof; and (b) at least one oncology therapeutic selected from a MEK inhibitor, an immune checkpoint inhibitor, a CDK inhibitor, an EGFR kinase inhibitor, an EGFR antibody, an EGFR PROTAC therapeutic, a FGFR inhibitor, a SOS1 inhibitor, a SHP2 inhibitor, a KRAS inhibitor, a taxane, a topoisomerase inhibitor, an ERK inhibitor, a platinum-based chemotherapy, folinic acid, 5-fluorouracil, or an anti-VEGF therapeutic. Another embodiment provides the method, wherein the at least one oncology therapeutic is a MEK inhibitor. Another embodiment provides the method, wherein the MEK inhibitor is selected from binimetinib, trametinib, cobimetinib, selumetinib, pimasertib, or mirdametinib. Another embodiment provides the method, wherein the at least one oncology therapeutic is an immune checkpoint inhibitor. Another embodiment provides the method, wherein the immune checkpoint inhibitor is a CTLA-4 inhibitor, a PD-1 inhibitor, or a PD-L1 inhibitor. Another embodiment provides the method, wherein the CTLA-4 inhibitor is ipilimumab. Another embodiment provides the method, wherein the PD-1 inhibitor is spartalizumab, nivolumab, pembrolizumab, or cemiplimab. Another embodiment provides the method, wherein the PD-L1 inhibitor is atezolizumab, avelumab, or durvalumab. Another embodiment provides the method, wherein the at least one oncology therapeutic is a CDK inhibitor. Another embodiment provides the method, wherein the CDK inhibitor is a CDK4/6 inhibitor. Another embodiment provides the method, wherein the CDK4/6 inhibitor is palbociclib, abemaciclib, or ribociclib. Another embodiment provides the method, wherein the at least one oncology therapeutic is an EGFR kinase inhibitor or antibody. Another embodiment provides the method, wherein the EGFR kinase inhibitor is nazartinib, gefitinib, erlotinib, afatinib, brigatinib, icotinib, neratinib, osimertinib, dacomitinib, or lapatinib. Another embodiment provides the method, wherein the EGFR antibody is cetuximab, panitumumab, zalutumumab, nimotuzumab, or matuzumab. Another embodiment provides the method, wherein the at least one oncology therapeutic is a SHP2 inhibitor. Another embodiment provides the method, wherein the at least one oncology therapeutic is a SOS1 inhibitor. Another embodiment provides the method, wherein the at least one oncology therapeutic is a FGFR inhibitor. Another embodiment provides the method, wherein the at least one oncology therapeutic is a KRAS inhibitor. Another embodiment provides the method, wherein the KRAS inhibitor is storasib, adagrasib, or BI-1701963. Another embodiment provides the method, wherein the at least one oncology therapeutic is a taxane. Another embodiment provides the method, wherein the at least one oncology therapeutic is a topoisomerase inhibitor. Another embodiment provides the method, wherein the topoisomerase inhibitor is irinotecan, topotecan, or belotecan. Another embodiment provides the method, wherein the at least one oncology therapeutic is an ERK inhibitor. Another embodiment provides the method, wherein the at least one oncology therapeutic is a platinum-based chemotherapy. Another embodiment provides the method, wherein the platinum-based chemotherapy is oxaliplatin, cisplatin, or carboplatin. Another embodiment provides the method, wherein the at least one oncology therapeutic is folinic acid. Another embodiment provides the method, wherein the at least one oncology therapeutic is 5-fluorouracil. Another embodiment provides the method, wherein the at least one oncology therapeutic comprises folinic acid and folinic acid. Another embodiment provides the method, further comprising the administration of a topoisomerase inhibitor or a platinum-based chemotherapy, or a combination thereof. Another embodiment provides the method, wherein the at least one oncology therapeutic is an anti-VEGF therapeutic. Another embodiment provides the method, wherein the anti-VEGF therapeutic is bevacizumab or aflibercept. Another embodiment provides the method, wherein the cancer is characterized as having an oncogenic BRAF alteration. Another embodiment provides the method, wherein the oncogenic BRAF alteration is a Class I BRAF mutation. Another embodiment provides the method, wherein the oncogenic BRAF alteration is a Class II BRAF mutation. Another embodiment provides the method, wherein the oncogenic BRAF alteration is a Class III BRAF mutation. Another embodiment provides the method, wherein the oncogenic BRAF alteration is a BRAF V600 mutation. Another embodiment provides the method, wherein the BRAF V600 mutation is a V600E or V600K mutation. Another embodiment provides the method, wherein the cancer is characterized as having a wild type BRAF. Another embodiment provides the method, wherein the cancer is a solid tumor. Another embodiment provides the method, wherein the cancer is an NRAS mutant tumor. Another embodiment provides the method, wherein the cancer is selected from melanoma, pancreatic cancer, pancreatic adenocarcinoma, ovarian cancer, colorectal cancer, glioma, Langerhans cell histiocytosis, leukemia, hairy cell leukemia, thyroid cancer, anaplastic thyroid cancer, papillary thyroid carcinoma, follicular thyroid carcinoma, or medullary thyroid carcinoma. Another embodiment provides the method, wherein the cancer is selected from small cell lung cancer, non-small cell lung cancer, prostate cancer, gastric cancer, and esophageal cancer. Another embodiment provides the method, wherein the cancer is selected from melanoma. Another embodiment provides the method, wherein the cancer is an NRAS mutant tumor. Another embodiment provides the method, wherein the cancer is pancreatic cancer. Another embodiment provides the method, wherein the cancer is pancreatic adenocarcinoma. Another embodiment provides the method, wherein the cancer is ovarian cancer. Another embodiment provides the method, wherein the cancer is colorectal cancer. Another embodiment provides the method, wherein the cancer is glioma. Another embodiment provides the method, wherein the cancer is Langerhans cell histiocytosis. Another embodiment provides the method, wherein the cancer is leukemia. Another embodiment provides the method, wherein the cancer is hairy cell leukemia. Another embodiment provides the method, wherein the cancer is thyroid cancer. Another embodiment provides the method, wherein the cancer is anaplastic thyroid cancer. Another embodiment provides the method, wherein the cancer is papillary thyroid carcinoma. Another embodiment provides the method, wherein the cancer is follicular thyroid carcinoma. Another embodiment provides the method, wherein the cancer is medullary thyroid carcinoma. Another embodiment provides the method, wherein the cancer is small cell lung cancer. Another embodiment provides the method, wherein the cancer is non-small cell lung cancer. Another embodiment provides the method, wherein the cancer is NRAS mutant non-small cell lung cancer. Another embodiment provides the method, wherein the cancer is NRAS mutant lung cancer. Another embodiment provides the method, wherein the cancer is prostate cancer. Another embodiment provides the method, wherein the cancer is gastric cancer. Another embodiment provides the method, wherein the cancer is cholangiocarcinoma. Another embodiment provides the method, wherein the cancer is esophageal cancer. Another embodiment provides the method, wherein the cancer is metastatic. Another embodiment provides the method, wherein the method is adjuvant therapy following surgical resection. Another embodiment provides the method, wherein the patient has relapsed after prior therapy. Another embodiment provides the method, wherein the patient has acquired resistance to prior therapy. Another embodiment provides the method, wherein the patient is refractory to therapy. Another embodiment provides the method, wherein the (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, is administered orally. Another embodiment provides the method, wherein the oral administration occurs every other day, once per day, twice per day, or three times per day.

Pharmaceutical Compositions

In certain embodiments, the heterocyclic RAF inhibitor described herein is administered as a pure chemical. In other embodiments, the heterocyclic RAF inhibitor described herein is combined with a pharmaceutically suitable or acceptable carrier (also referred to herein as a pharmaceutically suitable or acceptable excipient, a physiologically suitable or acceptable excipient, or a physiologically suitable or acceptable carrier) selected on the basis of a chosen route of administration and standard pharmaceutical practice.

Provided herein is a pharmaceutical composition comprising the heterocyclic RAF inhibitor as described herein, or a stereoisomer, pharmaceutically acceptable salt, hydrate, or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject or the patient) of the composition.

One embodiment provides a method of preparing a pharmaceutical composition comprising mixing the heterocyclic RAF inhibitor as described herein, or a stereoisomer, pharmaceutically acceptable salt, hydrate, or solvate thereof, and a pharmaceutically acceptable carrier.

Provided herein is the method wherein the pharmaceutical composition is administered orally. Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., *Remington: The Science and Practice of Pharmacy* (Gennaro, 21$^{st}$ Ed. Mack Pub. Co., Easton, PA (2005)).

Provided herein is the method wherein the pharmaceutical composition is administered by injection. In some embodiments, the heterocyclic RAF inhibitor as described herein, or pharmaceutically acceptable salt or solvate thereof, is formulated for administration by injection. In some instances, the injection formulation is an aqueous formulation. In some instances, the injection formulation is a non-aqueous formulation. In some instances, the injection formulation is an oil-based formulation, such as sesame oil, or the like.

The dose of the composition comprising the heterocyclic RAF inhibitor as described herein, or a stereoisomer, pharmaceutically acceptable salt, hydrate, or solvate thereof, differs depending upon the subject or patient's (e.g., human) condition. In some embodiments, such factors include general health status, age, and other factors. Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

EXAMPLES

These examples are provided for illustrative purposes only and not to limit the scope of the claims provided herein.

Example 1: RAF Inhibitory Activity of Compound 1

Methods

The inhibition of BRAF and RAF1 (CRAF) kinases by Compound 1 was measured by ADP-Glo assay in 17 and 18 independent experiments for BRAF and CRAF, respectively, as indicated in Table 1. In the assay, ATP is converted to ADP by the test kinase in the presence of substrate. The assay reagents then convert the remaining ADP to ATP and result in a luciferase reaction and luminescent readout proportional to the relative kinase activity. Compound 1 was diluted in DMSO were used in 10-point, 3-fold dose curves for both assays. A high dose of 1 μM and low dose of 0.05 nM were tested. Final concentrations of 6 nM BRAF (CarnaBio, Cat. 09-122) or 3 nM RAF1 (CarnaBio, Cat. 09-125) and 30 nM MEK1 substrate (Millipore, Cat. 14-420) were incubated with 3 μM ATP, 10 mM $MgCl_2$, 0.003% Brij-35, 2 mM DTT, 0.05% BSA, 1 mM EGTA, and 50 mM HEPES for 90 minutes at room temperature prior to addition of ADP-Glo reagent (Promega, Cat. V9102) for 40 minutes, and detection reagent (Promega, Cat. V9102) for 45 minutes. Luminescence was read on an Envision plate reader (PerkinElmer) and percent remaining activity was used to calculate $IC_{50}$ with a four parameter fit model using Dotmatics Knowledge Solutions Studies curve fitting software (Dotmatics, Bishops Stortford, UK, CM23).

TABLE 1

| Kinase | $IC_{50}$ (nM) | n | SEM (nM) |
|---|---|---|---|
| BRAF | 5.98 | 17 | 0.51 |
| RAF1 (CRAF) | 1.3 | 18 | 0.05 |

The Reaction Biology (Malvern, PA) kinase screening service uses transfer of radioactive $^{33}$P-labeled phosphate from ATP to kinase substrate to measure the effect of test compounds on kinase activity via its Kinase HotSpot Assay (Anastassiadis T et al 2011). Reactions were carried out at Km ATP 15 μM, 20 μM, 20 μM, and 10 μM for ARAF, BRAF, BRAF-V600E, and RAF1 (CRAF), respectively. Appropriate substrate was diluted in reaction buffer containing 20 mM HEPES (pH 7.5), 10 mM MgCl2, 1 mM EGTA, 0.01% Brij35, 0.02 mg/ml BSA, 0.1 mM Na3VO4, 2 mM DTT, 1% DMSO. Following kinase incorporation into the solution, Compound 1 was added in 10-point, 3 fold dose curves starting at 3 μM top dose and low dose of 0.152 μM for a 20 minute pre-incubation at room temperature. $^{33}$P-ATP was added into the reaction mixture to initiate the reaction and incubated for 2 hours at room temperature. Kinase activity was detected by P81 filter-binding method. $IC_{50}$ values were calculated using a four parameter fit model using Dotmatics Knowledge Solutions Studies curve fitting software (Dotmatics, Bishops Stortford, UK, CM23) and are provided in Table 2.

TABLE 2

| Kinase | $IC_{50}$ (nM) |
|---|---|
| ARAF | 2.41 |
| BRAF | 3.46 |
| BRAF V600E | 1.53 |
| RAF1 (CRAF) | 0.573 |

Compound 1 was tested at 1 μM ATP (where available) toward the human kinome in the Carna Biosciences Kinase Panel of 299 kinases by Carna Biosciences (Kobe, Japan) with the Caliper LabChip3000 assay (Caliper Life Science, Hopkinton, MA), which is a mobility shift assay that combines the basic principles of capillary electrophoresis in a micro-fluidic environment (Perrin et al 2010). The 4× Substrate/ATP/Metal solution was prepared with kit buffer (20 mM HEPES, 0.01% Triton X-100, 5 mM DTT, pH7.5), and 2× kinase solution was prepared with assay buffer (20 mM HEPES, 0.01% Triton X-100, 1 mM DTT, pH7.5). The 5 μL of 4× compound solution, 5 mL of 4× Substrate/ATP/Metal solution, and 10 mL of 2× kinase solution were mixed and incubated in a well of polypropylene 384 well microplate for 1 or 5 hour(s)* at room temperature. (*; depend on kinase). 70 mL of Termination Buffer (QuickScout Screening Assist MSA; Carna Biosciences) was added to the well. The reaction mixture was applied to LabChip™ system (Perkin Elmer), and the product and substrate peptide peaks were separated and quantitated. The kinase reaction was evaluated by the product ratio calculated from peak heights of product (P) and substrate (S) peptides (P/(P+S)). Kinases outside the RAF family inhibited >10% by 1 μM Compound 1 are listed in Table 3.

TABLE 3

| Kinase | % Inhibition 1 μM |
|---|---|
| DDR1 | 85.4 |
| DDR2 | 39.3 |
| HER4 | 30.9 |
| LOK | 17.9 |
| PKCepsilon | 16.9 |
| TYRO3 | 13.7 |
| PIM1 | 13.7 |
| HER2 | 12.6 |
| CHK1 | 11.6 |
| EGFR | 11.6 |
| TNIK | 11.3 |
| CSK | 10.6 |
| CaMK4 | 10.3 |
| SLK | 10.1 |

Conclusion

The biochemical potency and kinase selectivity of Compound 1 was determined using a suite of biochemical assays. The inhibition potency of Compound 1 on Rapidly Accelerated Fibrosarcoma (RAF) kinases were profiled in both the adenosine diphosphate (ADP)-Glo screening assay as well as radiometric kinase assays. Compound 1 was demonstrated to be a potent inhibitor of the RAF1, BRAF, ARAF kinases, with $IC_{50}$ values<5 nM. Non-RAF kinome selectivity was evaluated in the kinase panel as measured by mobility shift assay and revealed that only DDR1 and DDR2 were inhibited ≥40% at 1 μM. Taken together, Compound 1 is a potent, selective RAF inhibitor with minimal activity towards the rest of the kinome.

Example 2: Compound 1 Inhibits Cell Proliferation in Cell Culture

Compound 1 is a selective and potent inhibitor of RAF kinases designed to target Class II and III BRAF mutations, in addition to Class I BRAF mutations. Here, we evaluated the in vitro pharmacodynamic biomarker activity of Compound 1 across multiple cellular models representing four categories of BRAF mutational status: Class I (A-375), Class II (BxPC-3, OV-90, NCI-H2405), Class III (WM3629 and CAL12-T), and wild type (MIA PaCa-2, CHL, NCI-H358).

Methods

A-375, BxPC-3, OV-90, NCI-H2405, CAL-12T, MIA PaCa-2, NCI-H358, and CHL-1 cells were seeded at 8000 cells/well in 24 μl growth media in a 384-well plate and allowed to adhere at 37° C. with 5% $CO_2$ overnight. WM3629 cells were seeded at 1500 cells/well in 24 μl growth media in a 384-well plate and allowed to adhere at 37° C. with 5% $CO_2$ overnight. The following day, compounds were serially diluted into 10-point, 3-fold dilution curves in 384 well plates. Compound 1 was transferred to cell plates such that the final concentration range was 0.508 nM to 10 μM in 0.1% DMSO with 0.1% DMSO being used as negative control. Cells were incubated with Compound 1 for 1 hour at 37° C. with 5% $CO_2$. Cells were lysed by addition of 8 μl 4× lysis buffer provided with HTRF kit plus 1× protease/phosphatase inhibitor cocktail. 20 μl lysate was transferred to HTRF plate and 2.5 μl each of anti-ERK1/2-Europium/Terbium Cryptate and anti-phospho-ERK1/2 antibody solutions per manufacturer's instructions. HTRF plates were incubated overnight at room temperature prior to reading in HTRF mode with 665 nm/620 nm (donor/acceptor). $EC_{50}$ values were calculated using a dose-response regression curve fitting utilizing a four-parameter analytical method.

Compound 1 demonstrated a range of cellular activities across BRAF mutant and wild type models as determined by pERK biomarker pharmacodynamic modulation after 1 hour of treatment, as shown in Table 4A. In tumor cells bearing Class III BRAF alterations, models WM3629 and CAL-12T, Compound 1 had mean $EC_{50}$ values of 8.8 and 18.4 nM, respectively. Class II BRAF mutant models, BxPC-3, OV-90, and NCI-H2405, Compound 1 demonstrated mean $EC_{50}$ values of 50.7, 26.0, and 10.1 nM, respectively. Class I BRAF mutation-harboring cells, A-375, were the least responsive mutant class and had a mean $EC_{50}$ of 67.7 nM. In three wild type models, MIA PaCa-2, CHL-1, and NCI-H358, Compound 1 had mean $EC_{50}$ values of 685, 580, and 351 nM, respectively. Additional cellular activity is provided in Table 4B.

TABLE 4A

| | BRAF | Compound 1 | | |
|---|---|---|---|---|
| Cell line | Mut Class | EC50 (nM) | SEM | N |
| A-375 | I | 67.7 | 4.3 | 7 |
| BxPC-3 | II | 50.7 | 5.6 | 12 |
| OV-90 | II | 26.0 | 1.6 | 23 |
| NCI-H2405 | II | 10.1 | 1.9 | 5 |
| WM3629 | III | 8.8 | 0.7 | 22 |
| CAL-12T | III | 18.4 | 4.7 | 5 |
| MIA PaCa-2 | WT | 685 | 147 | 5 |
| CHL-1 | WT | 580 | 83 | 4 |
| NCI-H358 | WT | 351 | 19.4 | 17 |

TABLE 4B

| Cell line | Tumor type | BRAF Mut Class | RAS Mut | EC50 (nM) |
|---|---|---|---|---|
| COLO 800 | Melanoma | I | WT | 99.5 |
| Hs 294T | Melanoma | I | WT | 76.9 |
| SK-MEL-28 | Melanoma | I | WT | 107.1 |
| HMV-II | Melanoma | II | NRAS Q61K | 44.6 |
| SK-MEL-30 | Melanoma | III | NRAS Q61K | 95.9 |
| IPC-298 | Melanoma | WT | NRAS Q61L | 267.4 |
| SK-MEL-2 | Melanoma | WT | NRAS Q61R | 139.1 |
| AM-38 | Glioblastoma | I | WT | 41.4 |
| DBTRG-05MG | Glioblastoma | I | WT | 60.5 |
| 8505C | ATC | I | WT | 77.1 |
| IHH-4 | PTC | I | WT | 53.1 |
| NCI-H2087 | NSCLC | II | NRAS Q61K | 95.4 |
| NCI-H1666 | NSCLC | III | WT | 32.9 |
| Calu-6 | NSCLC | WT | KRAS Q61K | 199.9 |
| HCC1195 | NSCLC | WT | NRAS Q61L | 83.3 |

ATC, Anaplastic thyroid cancer; PTC, Papillary thyroid cancer; NSCLC, Non-small cell lung cancer Conclusions In summary, Compound 1 demonstrated a range of cellular activities across BRAF mutant and wild type models, as determined by pERK biomarker modulation. Class II and Class III mutant models demonstrated the most potent cellular responses when treated with Compound 1 while wild type BRAF models were the least responsive.

Example 3: Determination of Anti-Proliferative Activity in a Xenograft Model

Methods

Groups and treatments were started when the mean tumor volume reached 200-335 $mm^3$ as indicated in the results section. Mice were assigned to respective groups based on their starting tumor volume and body weight such that the average values were the same for each treatment group. The study groups and number of animals per group are shown in Tables 5-7.

A. Evaluation of Antitumor Activity of Compound 1 in Class I BRAF-Mutant Human Cancer The antitumor activity of Compound 1 was first evaluated in the human A-375 melanoma xenograft model harboring a Class I BRAF V600E mutation. Treatment with Compound 1 (15, 30, or 60 mg/kg; free base form) was initiated when tumor volumes reached approximately 200 $mm^3$ and was continued once daily (QD) for 3 weeks. Mean A-375 xenograft tumor volumes (FIG. 1A), mouse body weight (FIG. 1B), and percent change in xenograft tumor volumes at end of study relative to baseline (FIG. 1C) following treatment with Compound 1 are presented by dose cohort. Compound 1 treatment was initiated when tumor volumes reached an average of ~205 $mm^3$ and continued for 21 days at indicated doses (n=9 animals per group). Mean tumor volumes and body weights are plotted, respectively; error bars denote standard error of mean. Percent change in tumor volume was calculated using the following formula: (TVf−TV0)/TV0×100%; where TVf=final tumor volume (at end of treatment) and TV0=initial tumor volume (at beginning of treatment).

TABLE 5

| Group No. | Drug | No. Animals | Dose (mg/kg) | Volume (μL/g) | Route | Regimen | Duration |
|---|---|---|---|---|---|---|---|
| 1 | Vehicle | 9 | 0 | 10 | PO | QD | 21 days |
| 3 | Compound 1 | 9 | 15 | 10 | PO | QD | 21 days |
| 4 | Compound 1 | 9 | 30 | 10 | PO | QD | 21 days |
| 5 | Compound 1 | 9 | 60 | 10 | PO | QD | 21 days |

Figure 1B:
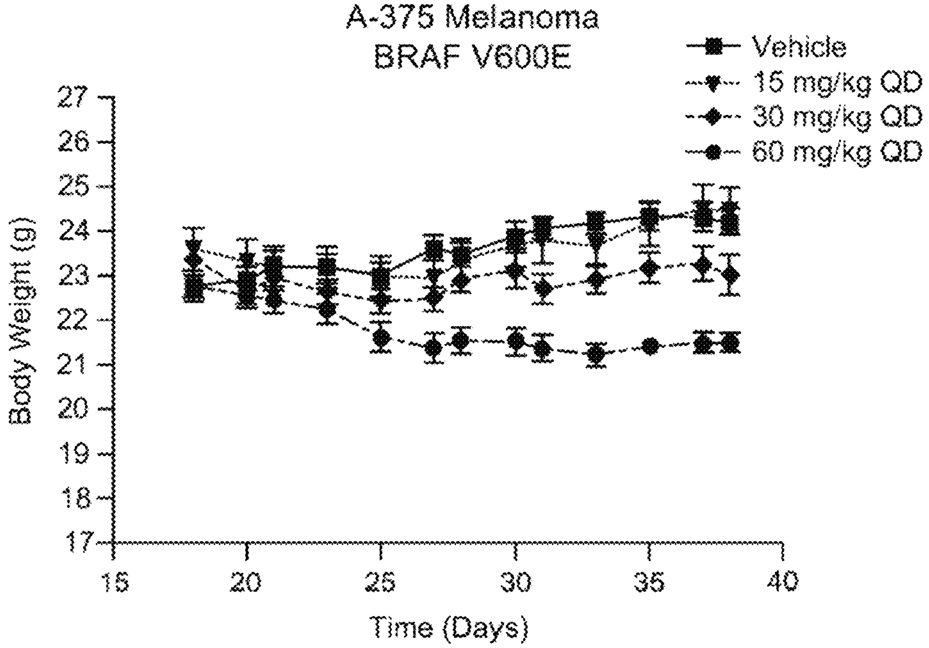

Compound 1 treatment resulted in systemic plasma exposures (AUClast) of 11,900-156,000 h*ng/mL when dosed orally over a 24-hour period following the last dose in mice bearing mutant A-375 BRAF Class I melanoma tumors. Dose-dependent inhibition of xenograft tumor growth relative to control (vehicle-treated) tumors was observed with Compound 1 treatment (FIG. 1A). All of the tested doses were well tolerated with some weight loss observed in animals treated with 60 mg/kg (average weight loss of 5.6%; FIG. 1B). One animal in the 60 mg/kg cohort had a weight loss>10% during the course of treatment but recovered by end of study.

Figure 1C:
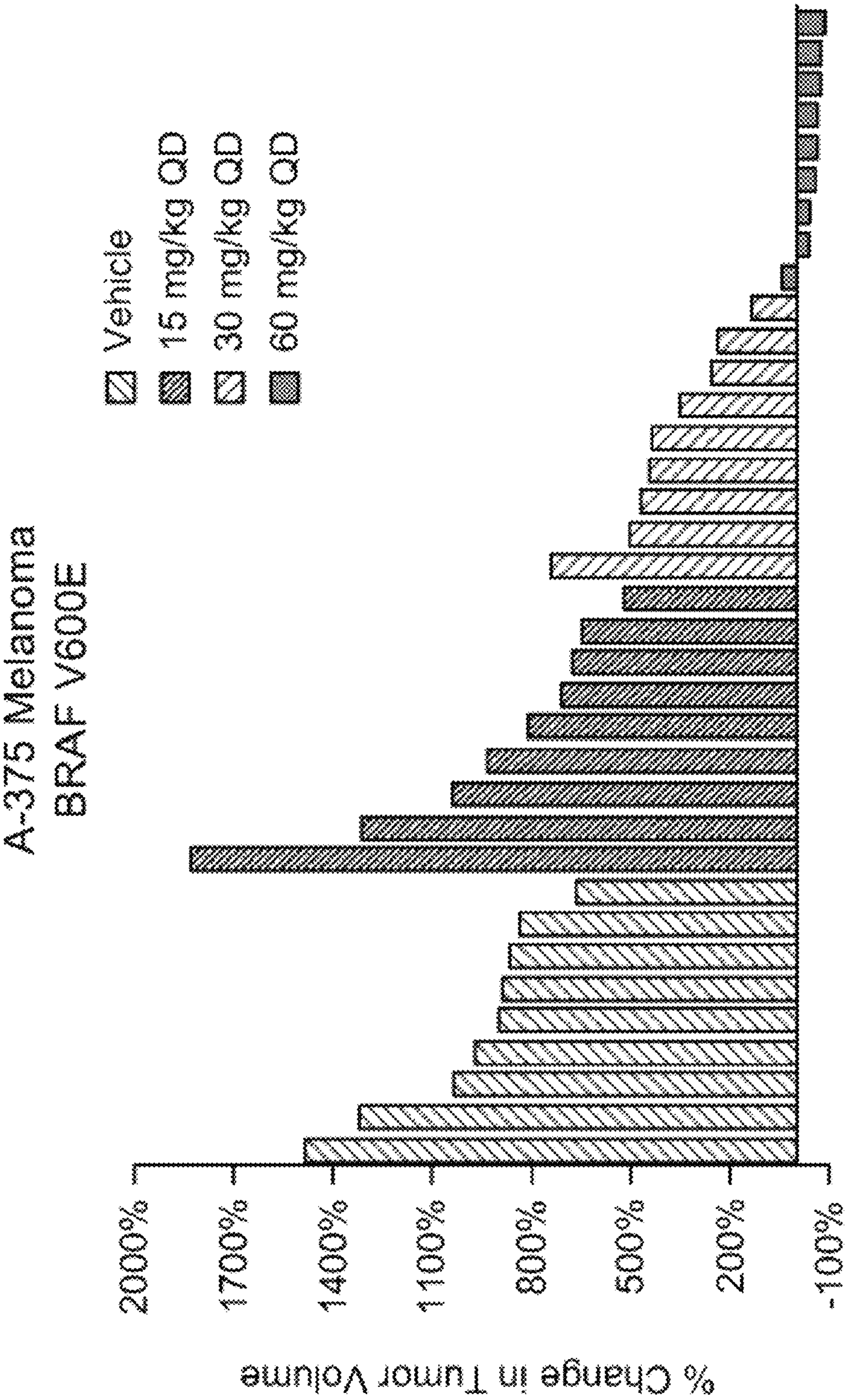

Waterfall plots of individual tumor response, defined as change in tumor volume from baseline are presented in FIG. 1C. The average TGI achieved with 30 mg/kg and 60 mg/kg daily doses, was 57% and 106%, respectively ($p \leq 0.0001$; FIG. 1C), with 8 of 9 animals in the latter group (89%) exhibiting tumor regressions. The lowest tested dose, 15 mg/kg, did not lead to significant TGI.

B. Evaluation of Antitumor Activity of Compound 1 in Class BRAF-Mutant Human Cancers The antitumor activity of Compound 1 was next evaluated in human xenograft models exhibiting Class II/III BRAF mutations. BxPC-3 pancreatic cancer and WM3629 melanoma cell-line derived xenografts harboring a Class II BRAF insertion-deletion (indel; V487_P492delinsA) and Class III BRAF D594G mutation, respectively, were treated with a total of 3-20 mg/kg daily of Compound 1 (sulfate salt form) for 2 weeks. Treatment was initiated when tumor volumes were ~240-280 $mm^3$ with animals receiving a range of equivalent total doses administered once (QD; 3-20 mg/kg) or twice (BID; 1.5-10 mg/kg) daily. Mean BxPC-3 (Class II BRAF mutant PDAC) and WM3629 (Class III BRAF mutant melanoma) xenograft tumor volumes (FIG. 2A, FIG. 2C) and mouse body weight (FIG. 2B, FIG. 2D) during treatment with Compound 1 are presented by dose cohort. Compound 1 treatment was initiated when tumor volumes reached an average of 240-283 $mm^3$ and continued for 14 days at indicated doses and frequencies (n=9 animals per group). Mean tumor volumes and body weights are plotted; error bars denote standard error of mean.

TABLE 6

| Group No. | Drug | No. Animals | Dose (mg/kg) | Volume (μL/g) | Route | Regimen | Duration |
|---|---|---|---|---|---|---|---|
| 1 | Vehicle | 9 | 0 | 10 | PO | BID | 14 days |
| 3 | Compound 1 | 9 | 1.5 | 10 | PO | BID | 14 days |
| 4 | Compound 1 | 9 | 3 | 10 | PO | BID | 14 days |
| 5 | Compound 1 | 9 | 5 | 10 | PO | BID | 14 days |
| 6 | Compound 1 | 9 | 10 | 10 | PO | BID | 14 days |
| 7 | Compound 1 | 9 | 3 | 10 | PO | QD | 14 days |
| 8 | Compound 1 | 9 | 6 | 10 | PO | QD | 14 days |
| 9 | Compound 1 | 9 | 10 | 10 | PO | QD | 14 days |
| 10 | Compound 1 | 9 | 20 | 10 | PO | QD | 14 days |

Figure 2A:
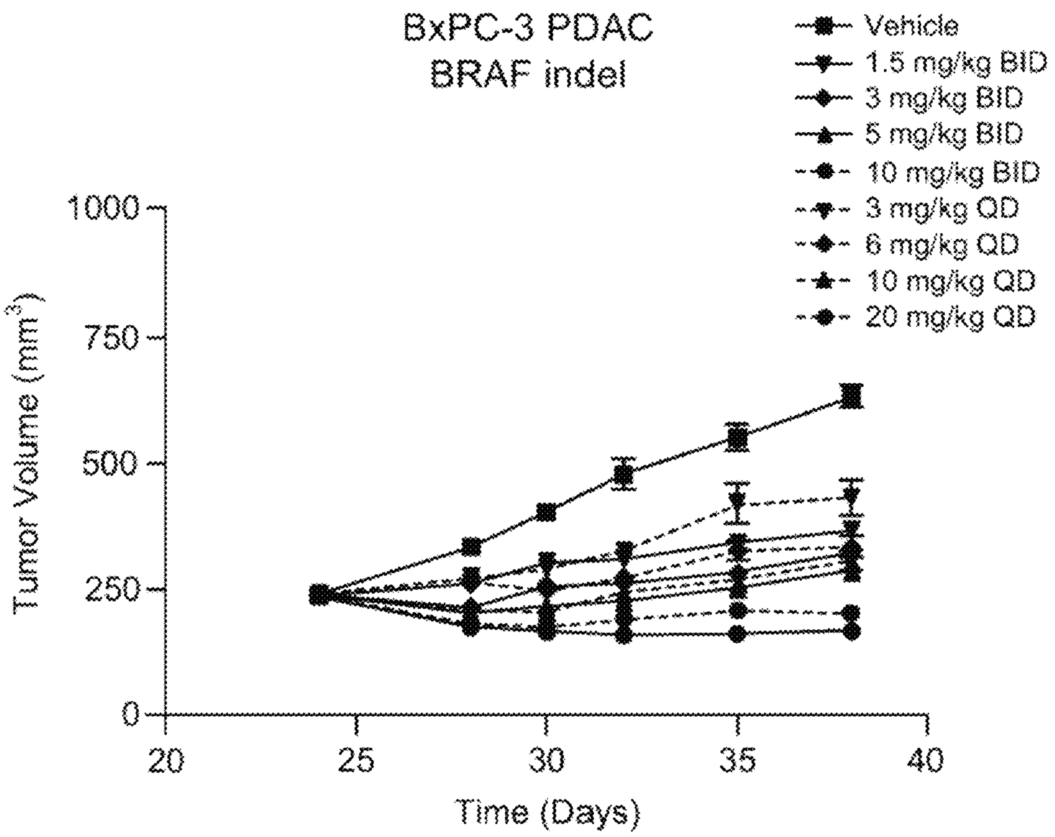
FIGS. 2A-2D illustrates BxPC-3 (Class II BRAF mutant PDAC) and WM3629 (Class III BRAF mutant melanoma) xenograft tumor volumes (FIG. 2A, FIG. 2C) and mouse body weight (FIG. 2B, FIG. 2D) during treatment with Compound 1.
Figure 2B:
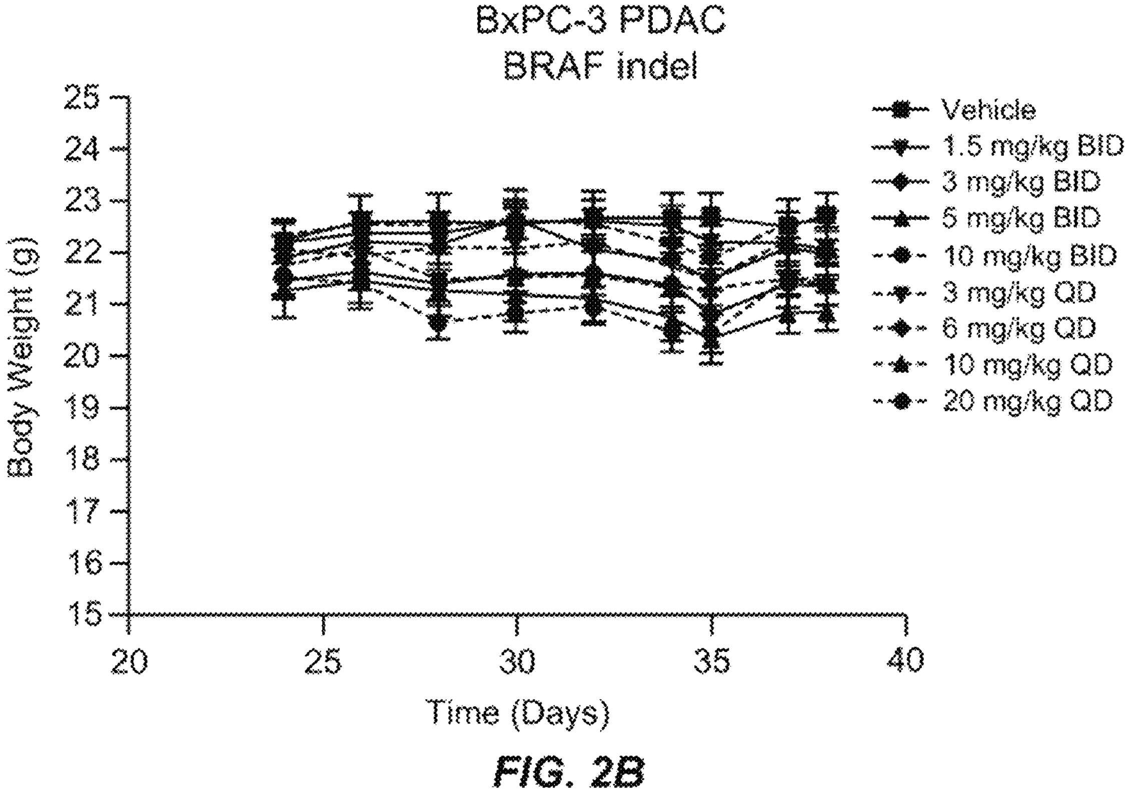
Figure 2C:
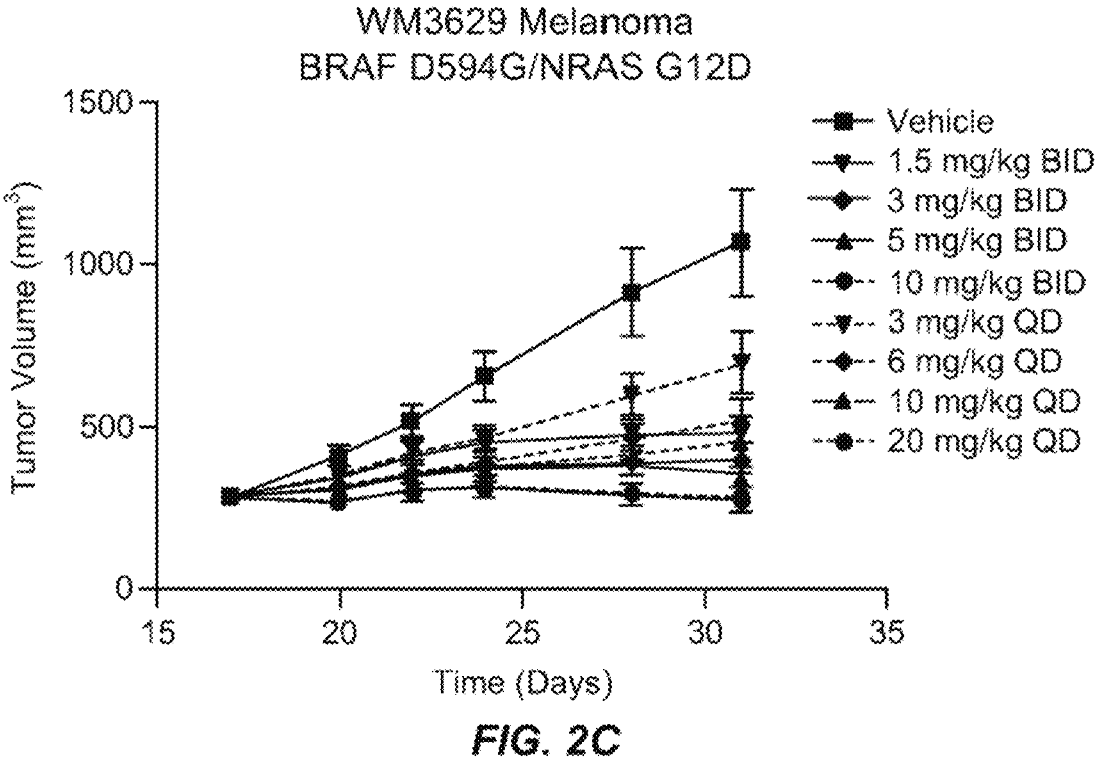
Figure 2D:
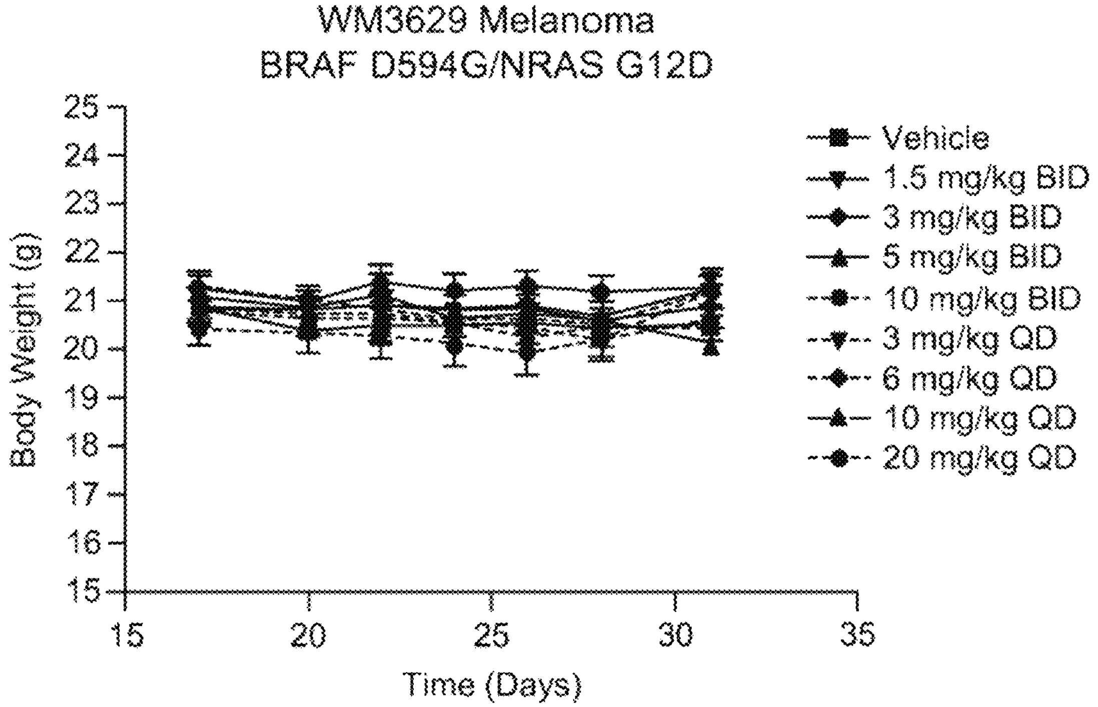

Compound 1 treatment resulted in systemic plasma exposures ($AUC_{last}$) of 4,030-42,100 h*ng/mL and 5,200-53,700 h*ng/mL when dosed orally BID or QD, respectively, over a 24-hour period following the last dose in mice bearing mutant BRAF Class II BxPC-3 pancreatic and Class III WM3629 melanoma xenografts. Dose-dependent inhibition of BxPC-3 and WM3629 xenograft tumor growth relative to control (vehicle-treated) tumors was observed with Compound 1 treatment (FIG. 2A, FIG. 2C). A trend towards greater TGI was achieved with BID, compared to QD, administration of equivalent total daily doses of Compound 1 in both models. All tested doses and schedules were well tolerated as measured by on-treatment animal body weight changes (FIG. 2B, FIG. 2D).

Figure 3A:
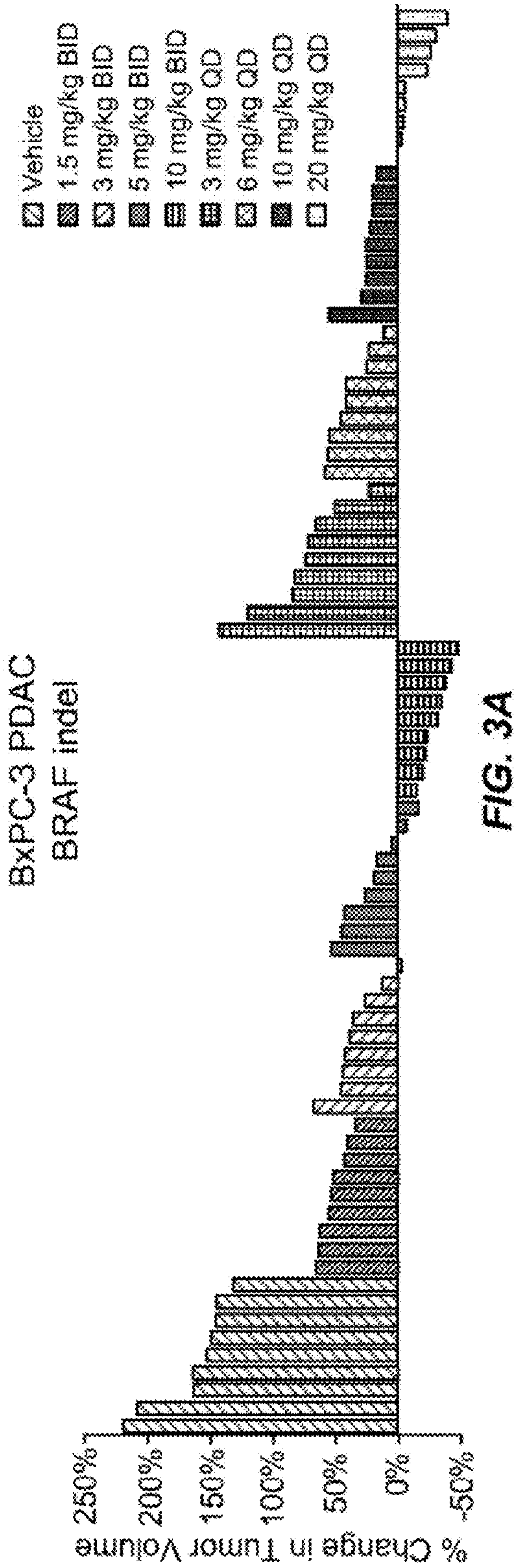
FIG. 3A and FIG. 3B illustrate waterfall plots of individual BxPC-3 tumor and WM3629 tumor xenograft responses are presented in FIG. 3A and FIG. 3B, respectively
Figure 3B:
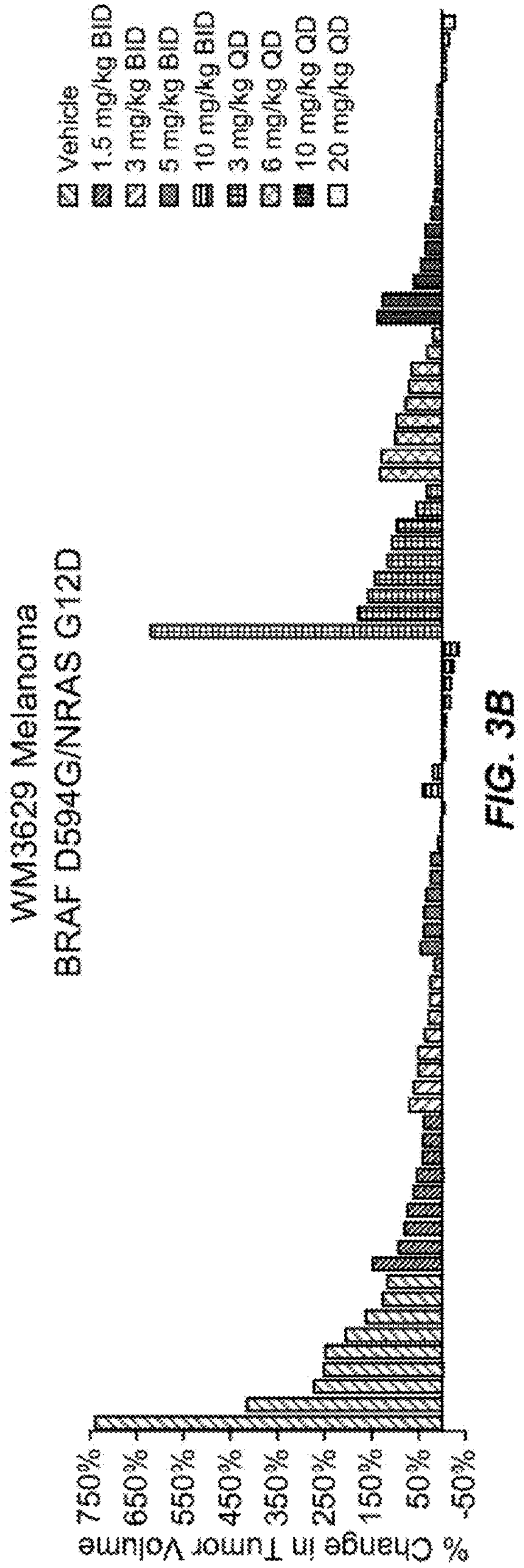

Waterfall plots of individual BxPC-3 tumor and WM3629 tumor xenograft responses are presented in FIG. 3A and FIG. 3B, respectively. Statistically significant reductions in BxPC-3 tumor growth were achieved at all tested doses up to 10 mg/kg total Compound 1 per day (51-88% inhibition; $p \leq 0.0001$; FIG. 3A). Additionally, tumor regressions were observed among animals in the 20 mg/kg QD and 3-10 mg/kg BID treatment groups (109% and 118% TGI at 20 mg/kg QD and 10 mg/kg BID, respectively; $p \leq 0.0001$). Similarly, TGI was observed with all tested doses and schedules in the WM3629 model (47-101% inhibition; $p \leq 0.04$-0.0001); with some cases of regression observed at the highest daily doses (FIG. 3B). Consistent with the BxPC-3 model, a regression was also achieved in one animal at a lower dose (5 mg/kg) when administered BID.

C. Evaluation of Antitumor Activity of Compound 1 in Combination With MEK Inhibition in Class III BRAF-Mutant Human Cancer The antitumor activity of Compound 1 when combined with binimetinib—a MEK inhibitor approved for use in combination with encorafenib for the treatment of advanced melanoma with BRAF V600E/K mutations—was evaluated in the human WM3629 (Class III BRAF mutant) melanoma xenograft model. Treatment with Compound 1 (15 or 30 mg/kg QD; free base form), binimetinib (10 mg/kg QD), and/or a combination of the two therapies was initiated when tumor volumes reached approximately 335 $mm^3$ and was continued once daily for 2 weeks.

TABLE 7

| Group No. | Drug | No. Animals | Dose (mg/kg) | Volume (μL/g) | Route | Regimen | Duration |
|---|---|---|---|---|---|---|---|
| 1 | Vehicle A | 9 | 0 | 10 | PO | QD | 14 days |
| 2 | Vehicle B | 9 | 0 | 10 | PO | QD | 14 days |
| 3 | binimetinib | 9 | 10 | 10 | PO | QD | 14 days |
| 8 | Compound 1 | 9 | 15 | 10 | PO | QD | 14 days |
| 9 | Compound 1 | 9 | 30 | 10 | PO | QD | 14 days |
| 14 | binimetinib + Compound 1 | 9 | 10/15 | 5/5 | PO/PO | QD/QD | 14 days |
| 15 | binimetinib + Compound 1 | 9 | 10/30 | 5/5 | PO/PO | QD/QD | 14 days |

Figure 4A:
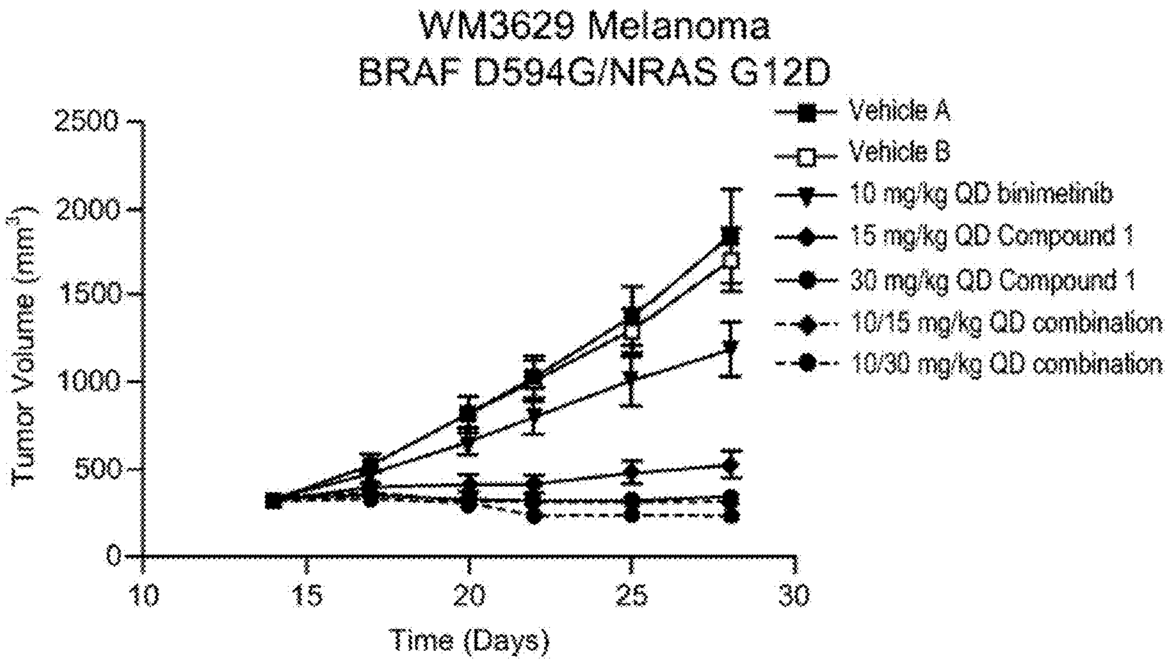
FIGS. 4A-C illustrates WM3629 tumor xenograft responses to combination therapy with Compound 1 and binimetinib as described in Example 3C.
Figure 4B:
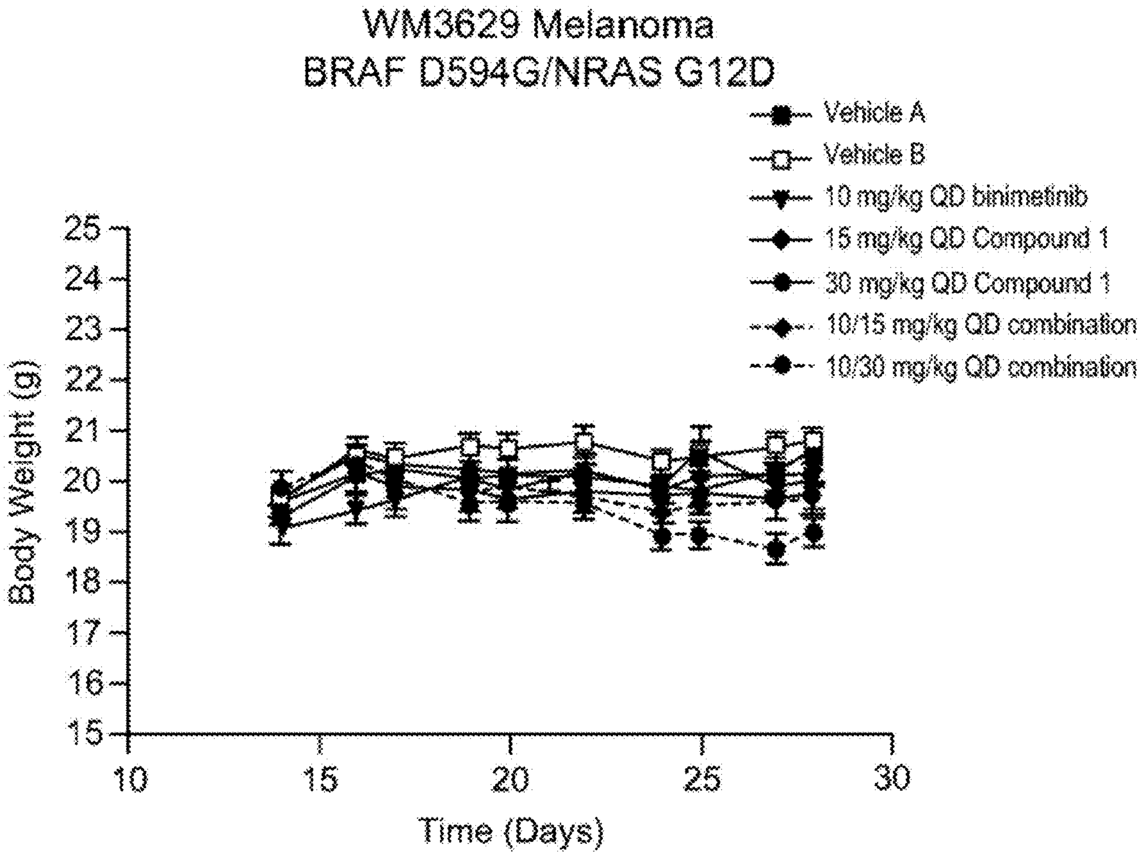
Figure 4C:
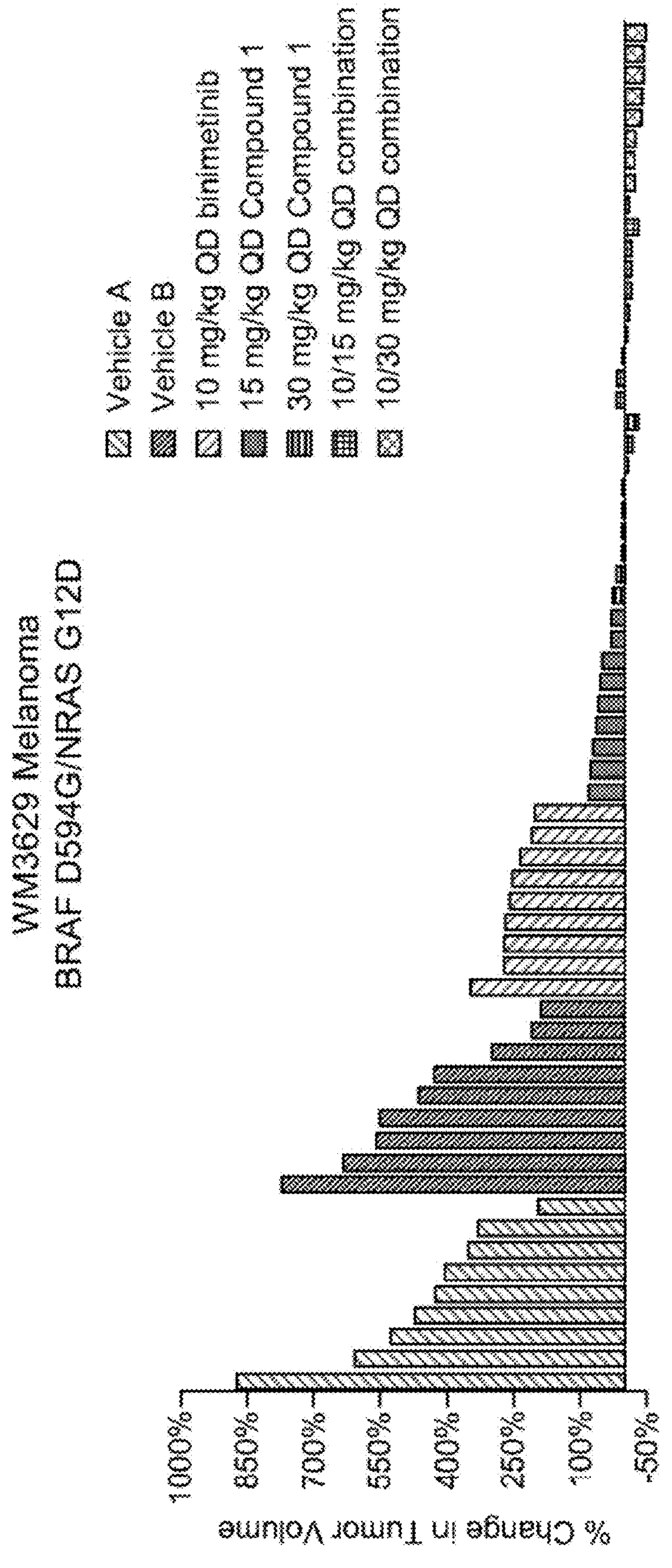

Systemic plasma exposures ($AUC_{last}$) ranging from 31,100-123,000 hr*ng/mL and 11,000-26,700 hr*ng/mL were achieved with Compound 1 and/or binimetinib treatment, respectively, at the tested doses. A dose-dependent response to Compound 1 monotherapy was observed (FIG. 4A, C). The average TGI was 86% and 99% with 15 mg/kg and 30 mg/kg, respectively. Treatment with binimetinib (10 mg/kg QD) as a single agent did not lead to significant inhibition of tumor growth. The addition of Compound 1 to binimetinib did, however, result in improved tumor xenograft growth inhibition with evidence of tumor regression (101% and 108% TGI with 10/15 mg/kg and 10/30 mg/kg binimetinib/Compound 1, respectively; p≤0.0001; FIG. 4C). Importantly, treatment with Compound 1 plus binimetinib was well-tolerated, with only one animal at the highest combination therapy dose exhibiting 10% body weight loss at a single on-treatment time point (FIG. 4B).

Conclusions

Compound 1 was well-tolerated and efficacious in athymic nude mouse xenograft models of BRAF-mutant human cancers at doses up to 60 mg/kg per day. Dose-dependent inhibition of A-375 (BRAF Class I mutation), BxPC-3 (BRAF Class II mutation), or WM3629 (BRAF Class III mutation) xenograft tumor growth was observed with daily Compound 1 treatment. A trend towards more robust tumor responses was observed with twice daily compared to once daily dosing of Compound 1, however, the two dosing regimens led to similar tumor growth inhibition (TGI) and regressions (mean TGI up to 101-118%; p≤0.0001) at equivalent total daily doses. Compound 1 was also well-tolerated and efficacious when combined with a MEK inhibitor leading to WM3629 xenograft tumor regressions (mean TGI 101-106%; p≤0.0001). These data indicate that Compound 1 has potent antitumor activity as a single agent and may also be safely combined with other targeted therapies for the treatment of BRAF-driven cancers.

Example 4: Evaluation of Cellular Activity of Compound 1 in Combination With Binimetinib in NRAS Mutant Melanoma Purpose: To evaluate the cellular potency and activity of Compound 1, a selective and potent inhibitor of rapidly accelerated fibrosarcoma (RAF) kinases, in combination with a mitogen-activated protein kinase kinase (MEK) inhibitor, binimetinib.

Figure 5:
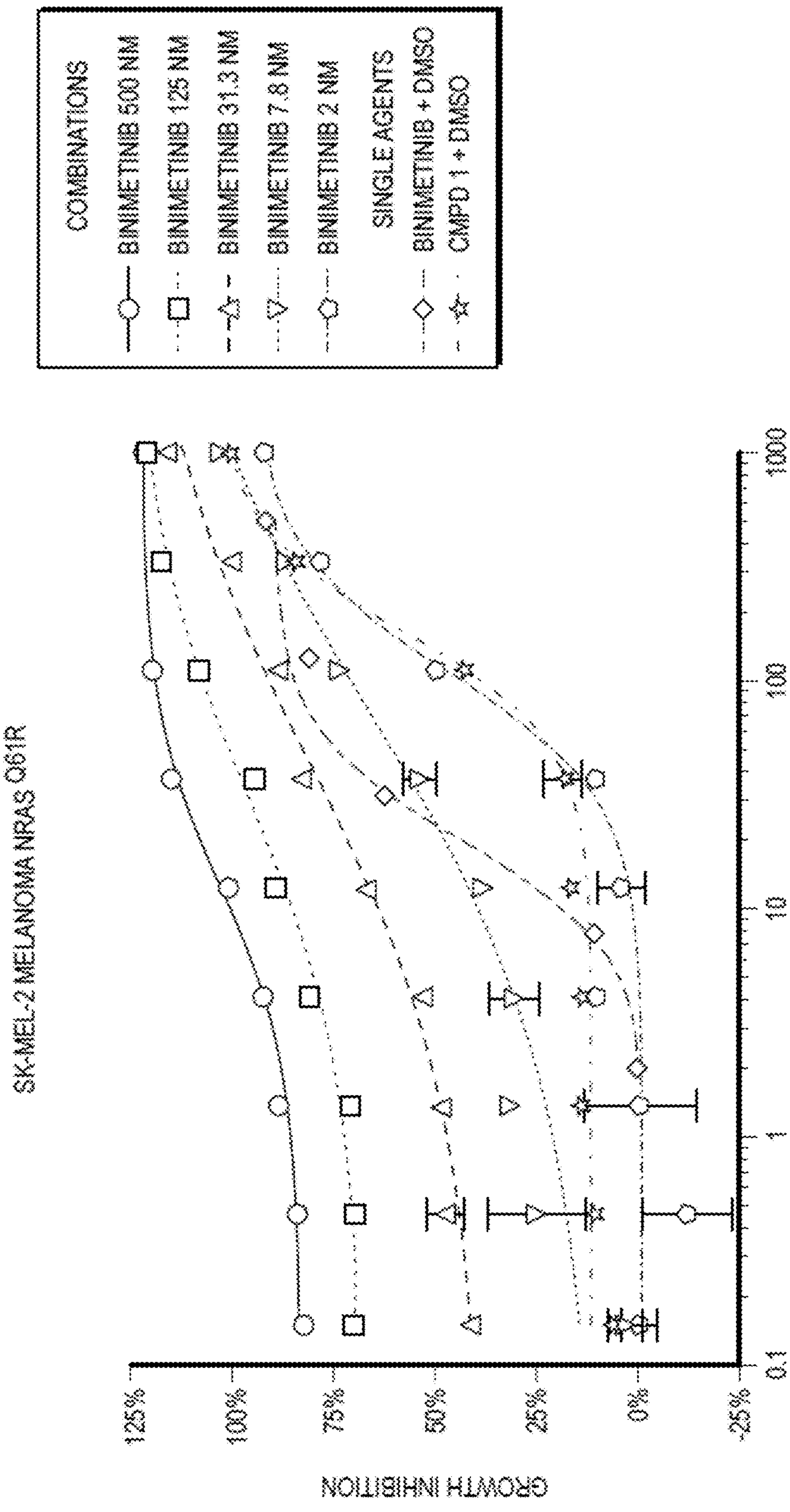
FIG. 5 illustrates the cellular activity of compound 1 in combination with binimetinib in NRAS mutant melanoma as described in Example 4.

Methods: Combinatorial activity of the RAF inhibitor Compound 1 plus binimetinib was evaluated in human neuroblastoma rat sarcoma viral oncogene homolog (NRAS) mutant melanoma cells in a 7-day growth assay. SK-MEL-2 human melanoma cells were obtained from American Type Culture Collection and maintained in DMEM+10% FBS+1% penicillin/streptomycin. All cells were maintained in a humidified incubator at 37° C. with 5% carbon dioxide ($CO_2$). SK-MEL-2 cells were seeded at 1,000 cells/well in 96 μL growth medium in a 96-well plate (Corning 3904) and allowed to adhere at 37° C. with 5% $CO_2$ overnight. The following day, Compound 1 was serially diluted in dimethyl sulfoxide (DMSO) into 9-point, 3-fold dilution curves in a 96-well plate starting from 1 mM. Binimetinib was serially diluted in DMSO into 5-point, 4-fold dilution curves in a 96-well plate starting from 500 μM. Then 2 μL of each compound was transferred to 196 μL of medium to make a 10× working dilution. 10 μL of working dilution was dispensed to the corresponding wells in 96-well plates to bring the total volume up to 100 μL. A 0.2% solution of DMSO was employed as negative control. Cells were incubated with compounds for 7 days at 37° C. with 5% $CO_2$. Plates were removed from the incubator and equilibrated at room temperature for 15 minutes. Then, 100 μL of CellTiter-Glo (CTG) reagent was added into each well to be detected (at 1:1 to culture medium). The plates were kept at room temperature for 30 minutes followed by reading on a plate reader. $EC_{50}$ values were calculated using a dose-response regression curve fitting utilizing a 4-parameter analytical method. Synergy analyses of the data were performed to assess the potential synergistic combination benefit for Compound 1 and binimetinib (Meyer et al. 2019, Ianevski et al. 2020). Single agent compound 1 (with DMSO control) resulted in a growth inhibitory $EC_{50}$ of 164 nM. When combined with increasing concentrations of binimetinib, compound 1 potency was enhanced, shifting $EC_{50}$ values to 108 nM, 106 nM, 65 nM, 39 nM, and 12 nM for binimetinib concentrations of 2, 7.8, 31.3, 125, and 500 nM, respectively, as illustrated in Table 8 and FIG. 5. This cellular study demonstrates a combination benefit when a MEK inhibitor, binimetinib, is added to compound 1 treatment in a human NRAS mutant melanoma cell line.

TABLE 8

| Cell Line | MAPK Alteration | Binimetinib Concentration (nM) | Compound 1 7-Day CTG $EC_{50}$ (nM) |
|---|---|---|---|
| SK-MEL-2 | BRAF wild type, NRAS_Q61R | 0 | 164 |
| | | 2 | 108 |
| | | 7.8 | 106 |
| | | 31.3 | 65 |
| | | 125 | 39 |
| | | 500 | 12 |

Potential synergy between compound 1 and binimetinib in the SK-MEL-2 cells was assessed using multiple available synergy models. The multi-dimensional synergy of combinations (MuSyC) model takes into account both potency (alpha) and efficacy (beta) in its model; scores>0 indicate synergy between the two drugs in the indicated parameter. Highest single agent (HSA), Bliss, and Loewe synergy models were assessed and utilized to find the most synergistic area score, where scores>10 indicate that the interaction between the two drugs is likely to be synergistic. The results from the 7-day growth assay were analyzed using multiple synergy models, see Table 9. The MuSyC model resulted in a beta score of 0.44 and an alpha score of 10.61, indicating both synergistic combination efficacy and synergistic potency in the SK-MEL-2 study. HSA, Bliss, and Loewe models calculated most synergistic area scores corresponding to 21.6, 16.2, and 11.6, respectively, indicating synergy in the ranges shown in Table 9. Taken together, this cellular study and subsequent synergy analyses demonstrate a synergistic combination benefit between compound 1 and binimetinib in the SK-MEL-2 human NRAS mutant melanoma cell line.

TABLE 9

| Synergy Model | Metric | Score |
|---|---|---|
| MuSyC | Alpha score (potency) | 10.61 |
| | Beta score (efficacy) | 0.44 |
| HSA | Most synergistic area score (binimetinib: 31.2-500 nM; compound 1: 111.1-1000 nM) | 21.6 |
| Loewe | Most synergistic area score (binimetinib: 7.8-125 nM; compound 1: 37-333.3 nM) | 16.2 |
| Bliss | Most synergistic area score (binimetinib: 7.8-125 nM; compound 1: 12.3-111.1 nM) | 11.6 |

Summary of Results: Compound 1 demonstrated potent inhibition of NRAS mutant human melanoma tumor cell models, as evidenced by inhibition of cell proliferation in a 7-day growth assay. Compound 1 growth inhibition potency was enhanced by combination with the MEK inhibitor binimetinib, as evidenced by decreasing half-maximal efficacious concentration (EC50) values with increasing doses of binimetinib.

Example 5: Evaluation of Antitumor Activity of Compound 1 in Combination With MEK Inhibition in NRAS-Mutant Human Melanoma The antitumor activity of Compound 1 when combined with binimetinib was evaluated in the human SK-MEL-2 (NRAS Q61R mutant) melanoma xenograft model. Treatment with Compound 1 (10 or 30 mg/kg BID), binimetinib (3 mg/kg BID), or a combination of the two therapies was initiated when tumor volumes reached approximately 307 $mm^3$ and was continued twice daily for 4 weeks.

TABLE 10

| Group No. | Drug | No. Animals | Dose (mg/kg) | Volume (mL/g) | Route | Regimen | Duration |
|---|---|---|---|---|---|---|---|
| 1 | Vehicle 1 + Vehicle 2 | 9 | 0 | 5 + 5 | PO | BID + BID | 28 days |
| 2 | Compound 1 | 9 | 10 | 10 | PO | BID | 28 days |
| 3 | Compound 1 | 9 | 30 | 10 | PO | BID | 28 days |
| 4 | Binimetinib | 9 | 3 | 5 | PO | BID | 28 days |
| 5 | Compound 1 + Binimetinib | 9 | 10 + 3 | 10 + 5 | PO | BID + BID | 28 days |

Figure 6:
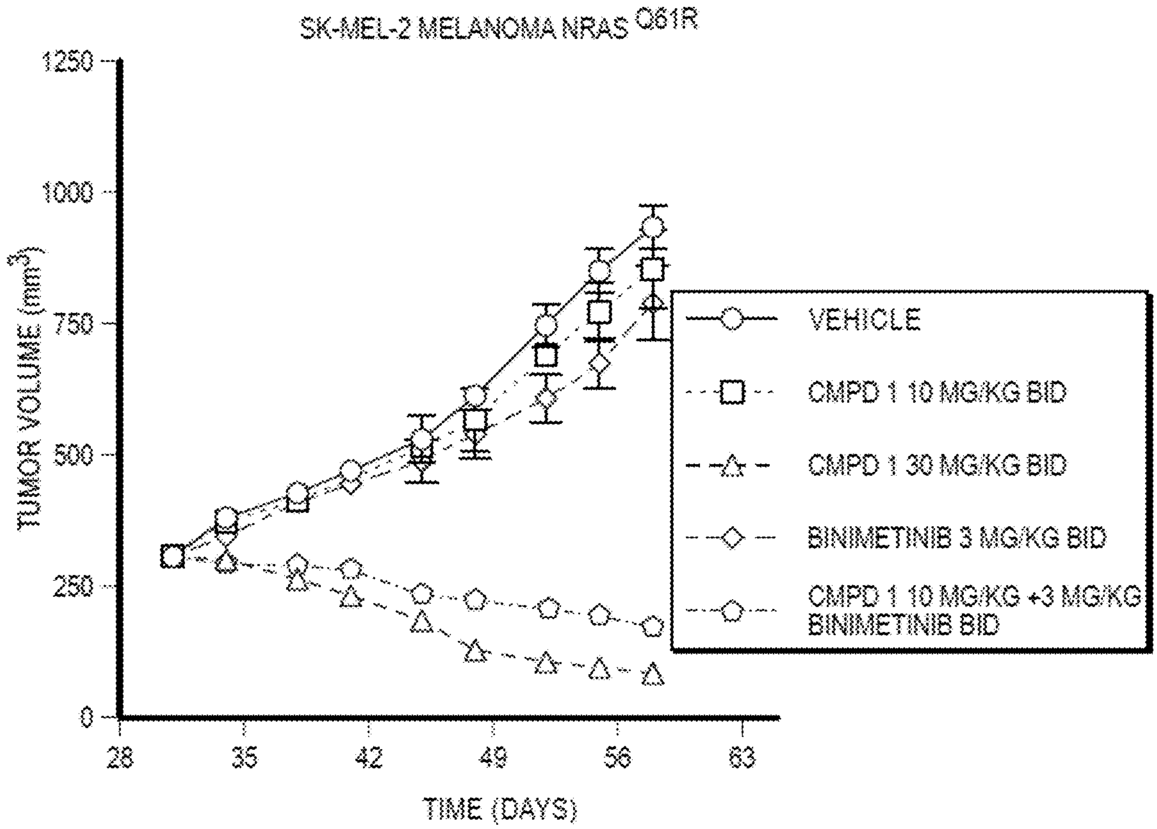
FIG. 6 illustrates the antitumor activity of compound 1 when combined with binimetinib in a human SK-MEL-2 (NRAS Q61R mutant) melanoma xenograft model as described in Example 5.
Figure 7:
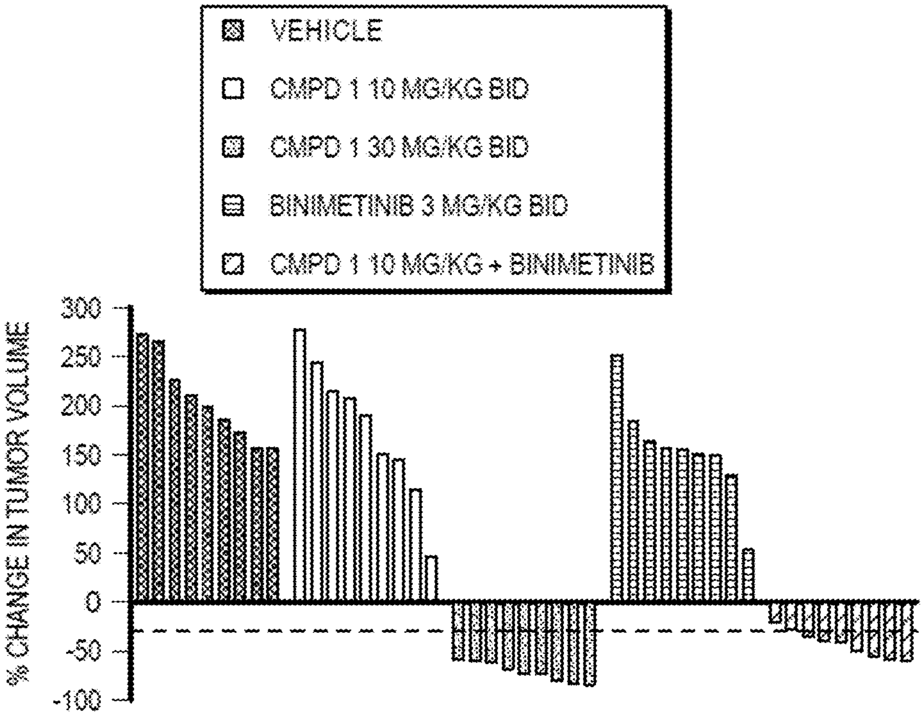
FIG. 7 illustrates the antitumor activity of compound 1 when combined with binimetinib in a human SK-MEL-2 (NRAS Q61R mutant) melanoma xenograft model as described in Example 5.

Systemic plasma exposures ($AUC_{0-24}$) ranging from 29,900-96,100 hr*ng/mL and 7,500-10,100 hr*ng/mL were achieved with Compound 1 and/or binimetinib treatment, respectively, at the tested doses. Tumor growth inhibition of monotherapy and combination groups was observed (FIG. 6). The average TGI was 13% and 135% with 10 mg/kg and 30 mg/kg, respectively. Treatment with binimetinib (3 mg/kg BID) as a single agent led to 23% tumor growth inhibition. The addition of 10 mg/kg Compound 1 to binimetinib resulted in improved tumor xenograft growth inhibition with evidence of tumor regression (122% with 10/3 mg/kg binimetinib/Compound 1, respectively; FIG. 7).

Example 6: Evaluation of Antitumor Activity of Compound 1 in Combination With Binimetinib in an NRAS Mutant, BRAF Mutant Melanoma Xenograft Model Purpose: To evaluate the tolerability and antitumor activity of compound 1, a selective and potent inhibitor of rapidly accelerated fibrosarcoma (RAF) kinases, plus a mitogen-activated protein kinase kinase (MEK) inhibitor, binimetinib, in a neuroblastoma rat sarcoma viral oncogene homolog (NRAS) mutant and rapidly accelerated fibrosarcoma kinase homolog B (BRAF) mutant human cancer cell line-derived xenograft model.

Methods: Athymic BALB/c nude mice were inoculated subcutaneously on the right flank with 1×107 human cancer cells. Twice daily (BID) oral (PO) administration of compound 1 and/or binimetinib was initiated when tumor volumes (TV) reached approximately 300 $mm^3$ and continued for 2 weeks. Animals were monitored for tumor growth, body weight changes, and general health/behavior.

Groups and treatments were started when the mean TV reached approximately 300 $mm^3$. Mice were assigned to respective groups based on their starting TV and body weight such that the average values were the same for each treatment group. The study groups and number of animals per group are shown in Table 11.

TABLE 11

| Group Number | Drug | Number of Animals | Dose (mg/kg) | Volume (μL/g) | Route | Regimen | Duration |
|---|---|---|---|---|---|---|---|
| 1 | Vehicle | 9 | 0 | 5 | PO | BID | 14 days |
| 2 | compound 1 | 9 | 1.5 | 5 | PO | BID | 14 days |
| 3 | compound 1 | 9 | 3 | 5 | PO | BID | 14 days |
| 4 | binimetinib | 9 | 3 | 5 | PO | BID | 14 days |
| 5 | binimetinib/ compound 1 | 9 | 3/1.5 | 5/5 | PO/PO | BID/BID | 14 days |
| 6 | binimetinib/ compound 1 | 9 | 3/3 | 5/5 | PO/PO | BID/BID | 14 days |

Mice were inoculated subcutaneously on the right flank with $1\times10^7$ WM3629 cells in 0.1 mL of 1:1 medium/Matrigel for tumor development. The treatments were administered to the tumor-bearing mice according to the study designs shown in Table 12. For routine monitoring, all study animals were monitored for not only tumor growth but also any abnormalities of behavior and appearance such as mobility, food and water consumption, body weight, eye appearance, and any other abnormal observations. Any mortality and/or abnormal clinical signs were recorded. Body weights of all animals were measured and recorded every other day throughout the study. The measurement of tumor size was conducted with calipers and recorded three times during the first week and twice weekly during the second and third weeks. The TV ($mm^3$) was estimated using the formula: $TV=a\times b^2/2$, where "a" and "b" are long and short diameters of a tumor, respectively.

TGI was calculated using the following equations:

$$\%\ T/C = 100\% \times (TV_f - TV_0)_{treated}/(TV_f - TV_0)_{control}$$

$$\%\ TGI = (1 - T/C) \times 100\%$$

where "$TV_f$" and "$TV_0$" are the final TV (at end of treatment) and initial TV (at beginning of treatment), respectively.

Animals were euthanized if they showed obvious signs of severe distress and/or pain, lost significant body mass (body weight loss>20%), were unable to reach adequate food or water, were otherwise observed to be in a continuing deteriorating condition, or if the size of their tumor exceeded 2,500 $mm^3$. All animals in a given study arm were euthanized when the group average TV reached >2,500 $mm^3$.

Results: The antitumor activity of compound 1 when combined with binimetinib was evaluated in the human WM3629 (NRAS mutant, Class III BRAF mutant) melanoma xenograft model. Treatment with compound 1 (1.5 or 3 mg/kg twice daily [BID]), binimetinib (3 mg/kg BID), and/or a combination of the two therapies was initiated when TVs reached approximately 300 $mm^3$ (actual mean TV for all groups was 283 $mm^3$) and was continued BID for 2 weeks. $AUC_{0\text{-}last}$ values ranging from 2,530-6,750 hr*ng/mL and 5,400-5,730 hr*ng/mL were achieved with compound 1 and/or binimetinib treatment, respectively, at the tested doses. Neither compound 1 nor binimetinib exposure differed substantially when administered as a monotherapy versus in combination.

Figure 8A:
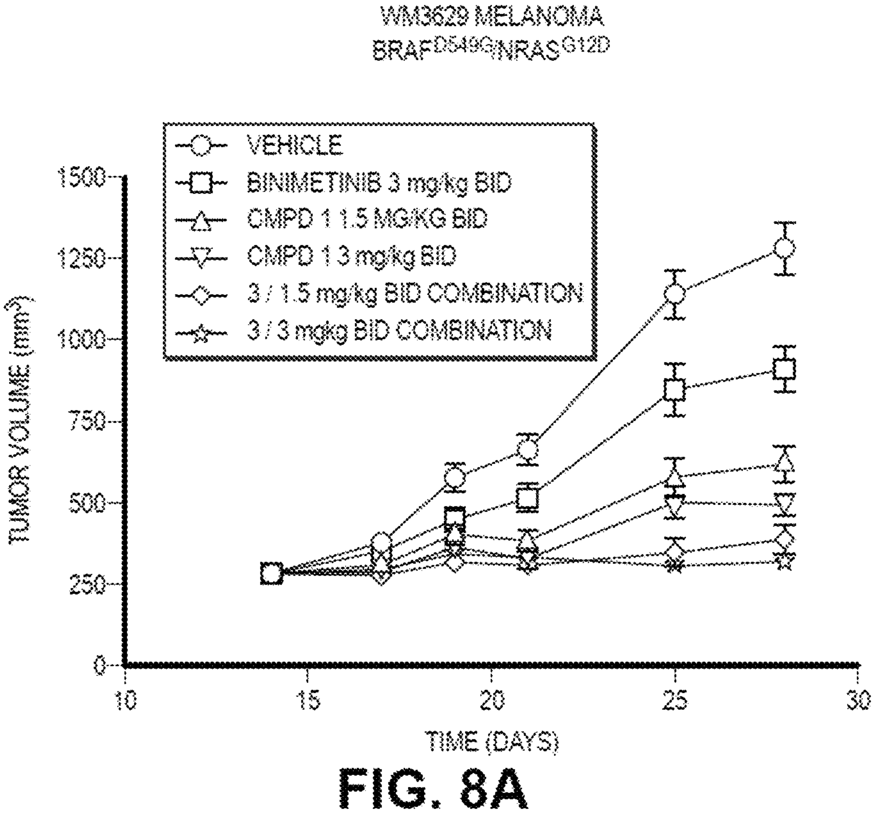
FIGS. 8A-8C illustrates the antitumor activity of compound 1 when combined with binimetinib in a WM3629 melanoma xenograft model as described in Example 6.
Figure 8B:
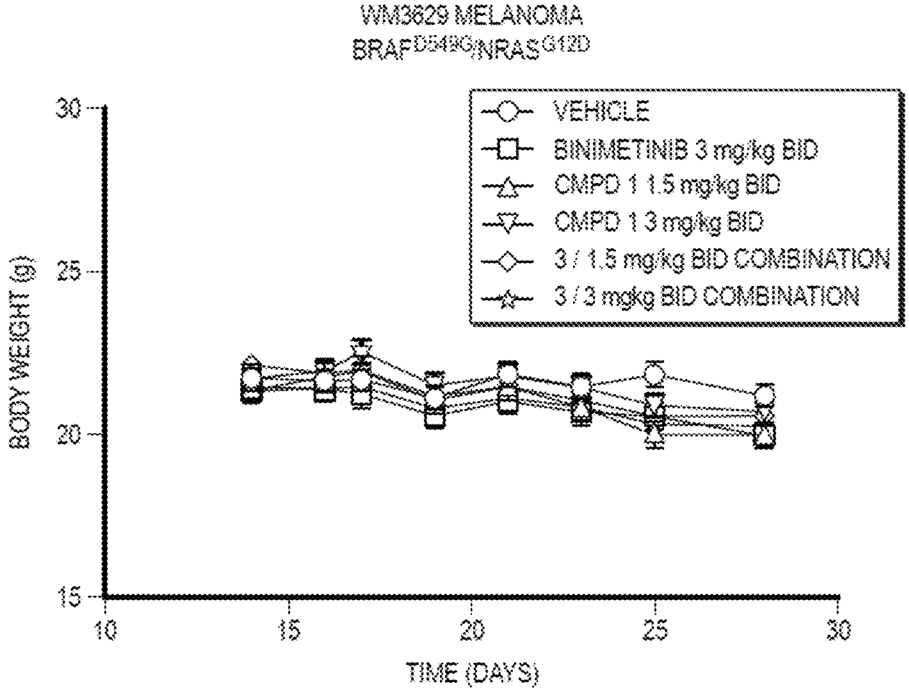
Figure 8C:
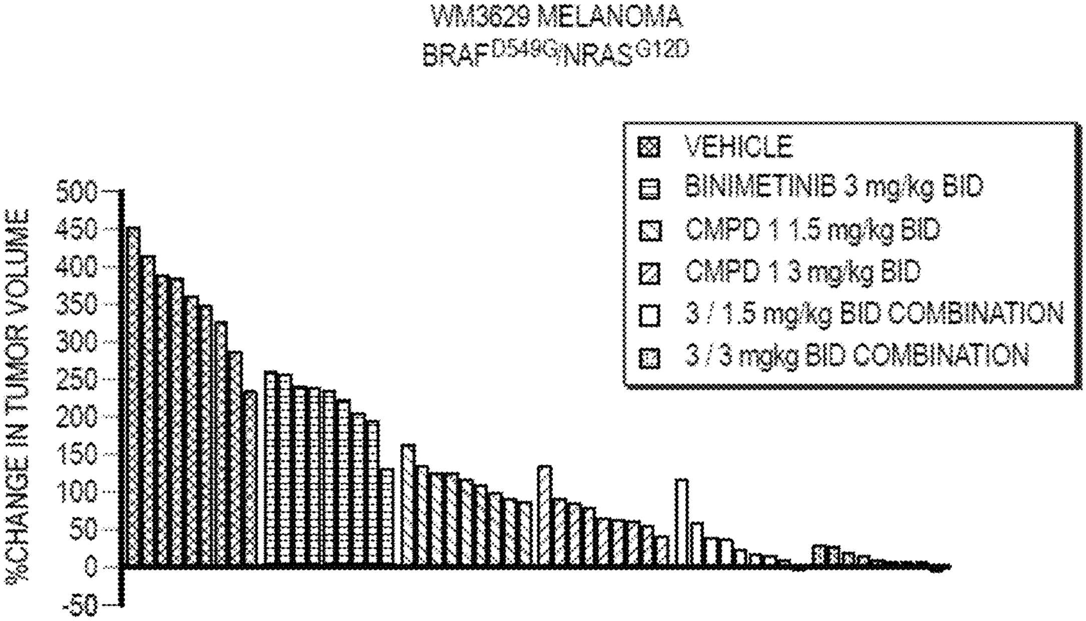

A dose-dependent response to compound 1 monotherapy was observed (FIGS. 8A and 8C). The average TGI was 66% and 79% with 1.5 mg/kg BID and 3 mg/kg BID compound 1, respectively (Table 13). Treatment with binimetinib (3 mg/kg BID) as a single agent led to an average TGI of 37% (FIGS. 8A and 8C; Table 13). The addition of compound 1 to binimetinib resulted in improved xenograft growth inhibition: 90% and 96% TGI with 3 mg/kg binimetinib/1.5 mg/kg compound 1 BID; and 3 mg/kg binimetinib/3 mg/kg compound 1 BID, respectively; FIGS. 8A and 8C; Table 13.

TGI was statistically significantly greater than in vehicle-treated animals after all treatments (p=0.0041 for binimetinib monotherapy, p<0.0001 for all other treatments; Table 12), and TGI after combination treatment with compound 1 and binimetinib was significantly greater than that seen with binimetinib monotherapy (p<0.0001 for both dose levels of combination therapy). Importantly, treatment with compound 1 plus binimetinib was well-tolerated, with only two animals at the 3 mg/kg binimetinib/1.5 mg/kg compound 1 BID dose level and no animals at the 3 mg/kg binimetinib/3 mg/kg compound 1 BID dose level exhibiting ≥10% body weight loss, see FIG. 8B.

TABLE 12

| Treatment | Baseline Tumor Volume ($mm^3$)[a] | Final Tumor Volume ($mm^3$)[a] | ΔT/ΔC (%)[b] | TGI (%)[c] | P-value[d] |
|---|---|---|---|---|---|
| Vehicle A + B | 283 ± 15 | 1281 ± 80 | — | — | — |
| 1.5 mg/kg BID compound 1 | 283 ± 14 | 618 ± 55 | 34 | 66 | <0.0001* |
| 3 mg/kg BID compound 1 | 283 ± 17 | 494 ± 35 | 21 | 79 | <0.0001* |
| 3 mg/kg BID binimetinib | 283 ± 17 | 910 ± 69 | 63 | 37 | 0.0041* |
| 3 mg/kg binimetinib/ 1.5 mg/kg compound 1 BID combination | 283 ± 16 | 387 ± 45 | 10 | 90 | <0.0001* |
| 3 mg/kg binimetinib/ 3 mg/kg compound 1 BID combination | 283 ± 15 | 320 ± 22 | 4 | 96 | <0.0001* |

ANOVA = analysis of variance; BID = twice daily; BRAF = rapidly accelerated fibrosarcoma homolog B; C = control; MEK = mitogen-activated protein kinase kinase; RM = repeated measures; SEM = standard error of the mean; T = treated; TGI = tumor growth inhibition; TV = tumor volume

[a]Mean ± SEM.

[b]$T/C = 100\% \times (TV_f - TV_0)_{treated}/(TV_f - TV_0)_{control}$ where $TV_f$ = final TV (at end of treatment) and $TV_0$ = initial TV (at beginning of treatment).

[c]TGI = (1−T/C) × 100%.

[d]P-value for the comparison of TGI in the respective treatment group vs. TGI in vehicle-treated animals, as determined by two-way RM ANOVA followed by Tukey's post hoc comparison of the means.

*P-values indicate statistically significant difference.

Summary of Results: Low dose compound 1 (1.5 or 3 mg/kg BID) was well-tolerated and efficacious as monotherapy or when combined with a MEK inhibitor, binimetinib (3 mg/kg BID), when dosed orally BID for 14 days in the NRAS mutant and BRAF mutant melanoma xenograft model, WM3629. Low dose compound 1 monotherapy led to moderate tumor growth inhibition (TGI; mean 66-79%), while combination of compound 1 with binimetinib led to significantly enhanced TGI (mean 90-96%; p<0.0001) when compared to binimetinib alone (mean TGI 37%). These data indicate that compound 1 may be safely and effectively combined with MEK inhibitor therapy for combination antitumor benefit in NRAS mutant melanoma.

Conclusions: Combined treatment with compound 1 and binimetinib, a MEK inhibitor, was well-tolerated and led to significant tumor inhibition in a xenograft model of NRAS mutant, Class III BRAF mutant melanoma, WM3629 (mean TGI of 90% and 96% with 3/1.5 mg/kg BID and 3/3 mg/kg BID binimetinib/compound 1, respectively). Tumor inhibition with compound 1/binimetinib combination treatment was significantly greater than with binimetinib monotherapy ($p<0.0001$). This study demonstrates antitumor combination benefit in adding a MEK inhibitor to compound 1 therapy in a human melanoma model bearing an NRAS mutation.

Example 7: Evaluation of the Antitumor Activity of Compound 1 in a BRAF Mutant NSCLC Xenograft Model Purpose: To evaluate the tolerability and antitumor activity of compound 1, a selective and potent inhibitor of rapidly accelerated fibrosarcoma (RAF) kinases in a RAF kinase homolog B (BRAF) mutant human non-small cell lung cancer (NSCLC) cell line-derived xenograft model.

Methods: Athymic mice were inoculated subcutaneously on the right flank with $1\times10^7$ human cancer cells. Twice daily (BID) oral (PO) administration of compound 1 was initiated when tumor volumes (TV) reached approximately 300 $mm^3$ and continued for 3 weeks. Animals were monitored for tumor growth, body weight changes, and general health/behavior.

Groups and treatments were started when the mean TV reached approximately 300 $mm^3$. Mice were assigned to respective groups based on their starting TV and body weight such that the average values were the same for each treatment group. The study groups and number of animals per group are shown in Table 13.

every other day throughout the study. The measurement of tumor size was conducted with calipers and recorded three times during the first week and twice weekly during the second and third weeks. The TV ($mm^3$) was estimated using the formula: $TV=a\times b^2/2$, where "a" and "b" are long and short diameters of a tumor, respectively.

TGI was calculated using the following equations:

$$\%\ T/C = 100\% \times (TV_f - TV_0)_{treated}/(TV_f - TV_0)_{control}$$

$$\%\ TGI = (1 - T/C) \times 100\%$$

where "$TV_f$" and "$TV_0$" are the final TV (at end of treatment) and initial TV (at beginning of treatment), respectively.

Animals were euthanized if they showed obvious signs of severe distress and/or pain, lost significant body mass (body weight loss>20%), were unable to reach adequate food or water, were otherwise observed to be in a continuing deteriorating condition, or if the size of their tumor exceeded 2,500 $mm^3$. All animals in a given study arm were euthanized when the group average TV reached >2,500 $mm^3$. Plasma and tumor tissue samples were collected for pharmacokinetic and pharmacodynamic analysis.

Results: The antitumor activity of compound 1 was evaluated in the human NCI-H2405 (Class II BRAF mutant) NSCLC xenograft model. Treatment with compound 1 (1.5, 3, 10, or 15 mg/kg twice daily [BID]) was initiated when TVs reached approximately 300 $mm^3$ (actual mean TV for all groups was 304 $mm^3$) and was continued BID for 3 weeks.

Dose-dependent exposures and antitumor responses to compound 1 treatment were observed. $AUC_{0-24}$ values ranging from 2878-50799 hr*ng/mL were achieved at the tested

TABLE 13

| Group Number | Drug | Number of Animals | Dose (mg/kg) | Volume (μL/g) | Route | Regimen | Duration |
|---|---|---|---|---|---|---|---|
| 1 | Vehicle | 9 | 0 | 10 | PO | BID | 21 days |
| 2 | Compound 1 | 9 | 1.5 | 5 | PO | BID | 21 days |
| 3 | Compound 1 | 9 | 3 | 5 | PO | BID | 21 days |
| 4 | Compound 1 | 9 | 10 | 5 | PO | BID | 21 days |
| 5 | Compound 1 | 9 | 15 | 5 | PO | BID | 21 days |

Figure 9A:
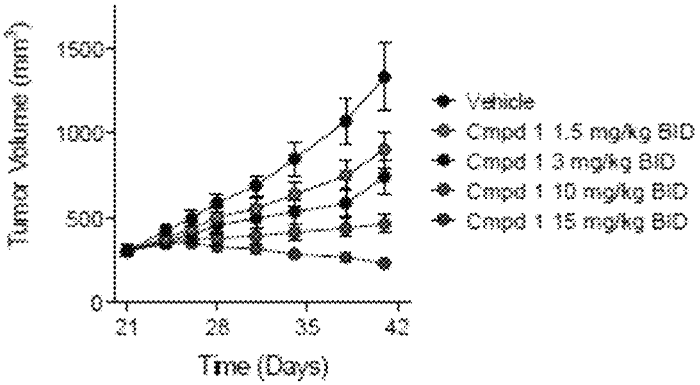
FIGS. 9A-9C illustrates the antitumor activity of compound 1 in a NSCLC xenograft model as described in Example 7.
Figure 9B:
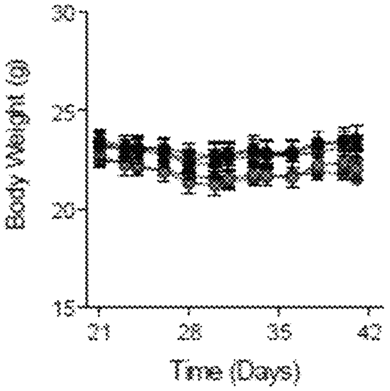
Figure 9C:
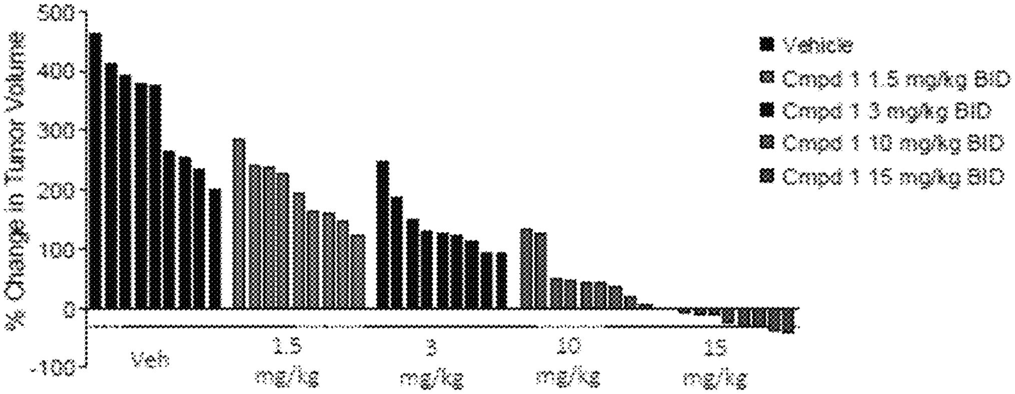

Mice were inoculated subcutaneously on the right flank with $1\times10^7$ NCI-H2405 cells in 0.1 mL of 1:1 medium/Matrigel for tumor development. The treatments were administered to the tumor-bearing mice according to the study designs shown in Table 13. For routine monitoring, all study animals were monitored for not only tumor growth but also any abnormalities of behavior and appearance such as mobility, food and water consumption, body weight, eye appearance, and any other abnormal observations. Any mortality and/or abnormal clinical signs were recorded. Body weights of all animals were measured and recorded doses, and tumor growth inhibition (TGI) relative to controls (vehicle-treated animals) was observed (FIG. 9A, FIG. 9C). The average TGI with increasing doses of 1.5, 3, 10, or 15 mg/kg BID was 42%, 58%, 85%, and 107%, respectively (Table 14). Statistically significant reductions in tumor growth were achieved at the 1.5, 3, 10, and 15 mg/kg BID doses of compound 1 ($p<0.0001$ for all comparisons; Table 14). Importantly, treatment with compound 1 was well-tolerated at all tested doses, with no groups exhibiting ≥10% body weight loss during the study (FIG. 9B).

TABLE 14

| Treatment | Baseline Tumor Volume ($mm^3$)[a] | Final Tumor Volume ($mm^3$)[a] | ΔT/ΔC (%)[b] | TGI (%)[c] | P-value[d] |
|---|---|---|---|---|---|
| Vehicle | 304 ± 31 | 1333 ± 199 | — | — | — |
| 1.5 mg/kg BID compound 1 | 304 ± 35 | 902 ± 105 | 58 | 42 | <0.0001* |

TABLE 14-continued

| Treatment | Baseline Tumor Volume ($mm^3$)[a] | Final Tumor Volume ($mm^3$)[a] | ΔT/ΔC (%)[b] | TGI (%)[c] | P-value[d] |
|---|---|---|---|---|---|
| 3 mg/kg BID compound 1 | 304 ± 32 | 741 ± 98 | 42 | 58 | <0.0001* |
| 10 mg/kg BID compound 1 | 304 ± 34 | 463 ± 53 | 15 | 85 | <0.0001* |
| 15 mg/kg BID compound 1 | 304 ± 33 | 230 ± 20 | −7 | 107 | <0.0001* |

ANOVA = analysis of variance; C = control; RM = repeated measures; SEM = standard error of the mean; T = treated; TGI = tumor growth inhibition; TV = tumor volume
[a]Mean ± SEM.
[b]$\Delta T/\Delta C = 100\% \times (TV_f - TV_0)_{treated}/(TV_f - TV_0)_{control}$ where $TV_f$ = final TV (at end of treatment) and $TV_0$ = initial TV (at beginning of treatment).
[c]TGI = (1−T/C) × 100%.
[d]P-value for the comparison of TGI in the respective treatment group vs. TGI in vehicle-treated animals, as determined by two-way RM ANOVA followed by Tukey's post hoc comparison of the means.
*P-values indicate statistically significant difference.

Summary of Results: Compound 1 (1.5 to 15 mg/kg BID) was well-tolerated and efficacious when dosed orally for 21 days in the BRAF mutant NSCLC xenograft model, NCI-H2405. Dose-dependent tumor growth inhibition (TGI) was observed with twice daily (BID) compound 1 treatment, with low dose compound 1 (1.5-3.0 mg/kg BID) leading to moderate TGI (mean 42-58%) and higher compound 1 doses (10-15 mg/kg BID) to strong TGI (mean 85-107%). TGI in all compound 1-treated groups differed statistically significantly from vehicle-treated animals (p<0.0001). These data indicate that compound 1 may be safely and effectively used for potent antitumor benefit in BRAF mutant NSCLC.

Example 8: Use of Compound 1 in a Human Clinical Trial

Title: A Phase 1/1b Open-Label, Multicenter Study to Investigate the Safety, Tolerability, Pharmacokinetics, and Antitumor Activity of compound 1 in Participants with BRAF and/or NRAS Mutation-positive Solid Tumors Study Phase: Phase 1/1b Indication: BRAF Mutation Positive Solid Tumors and/or NRAS mutation-positive solid tumors Introduction: This is a 2-part, open-label, multicenter, dose escalation and dose expansion study in participants with rapidly accelerated fibrosarcoma, homolog B (BRAF) mutation-positive and/or neuroblastoma RAS (NRAS) mutation-positive tumors designed to evaluate the safety, tolerability, and pharmacokinetics (PK) of compound 1, a pan-rapidly accelerated fibrosarcoma (RAF) small molecule kinase inhibitor; to determine a recommended Phase 2 dose (RP2D) of compound 1 for further clinical development; and to assess the objective response to compound 1 therapy alone and in combination with binimetinib, a mitogen-activated protein kinase (MEK) inhibitor.

Study Objectives

Part A: The primary objectives of the Part A Dose Escalation compound 1 Monotherapy component (hereafter referred to as Part A1) of the study are to determine the safety and tolerability of oral administration of compound 1 including dose-limiting toxicities (DLTs) in participants with BRAF mutation-positive advanced or metastatic solid tumors or melanoma harboring an NRAS mutation, and to identify the maximum tolerated dose (MTD) and/or the appropriate dose for further clinical investigation in Part B Dose Expansion. Secondary objectives include characterization of PK properties and effect of food on PK of compound 1. The primary objectives of the Part A Dose Escalation: compound 1+Binimetinib Combination component (hereafter referred to as Part A2) of the study are to determine the safety and tolerability of oral administration of compound 1+binimetinib including DLTs in participants with BRAF Class II or III mutation-positive advanced or metastatic solid tumors or melanoma harboring an NRAS mutation, and to identify the MTD and/or the appropriate dose for further clinical investigation. The secondary objective includes characterization of PK properties of compound 1 and binimetinib in combination.

Part B: The primary objective of the Part B Dose Expansion portion of the study is to assess preliminary evidence of the anti-cancer activity of compound 1 in participants with advanced or metastatic solid cancers harboring either a Class II or Class III BRAF genomic alteration. The secondary objective includes further evaluation of the safety, tolerability, and PK of compound 1 at the RP2D.

Study Design

The study will be conducted in 2 parts. Part A comprises 2 components: 1) Dose Escalation: compound 1 Monotherapy (Part A1); and 2) Dose Escalation: compound 1+Binimetinib Combination (Part A2). Part B Dose Expansion will assess preliminary evidence of the anti-cancer activity of compound 1 in participants with advanced or metastatic solid cancers.

Part A (Dose Escalation)

In Part A, participants with solid tumors harboring any BRAF Class I, Class II, or Class III mutation and/or NRAS-mutation positive melanoma will be included, subject to meeting all protocol-defined eligibility requirements. The number of participants with tumors with BRAF Class I mutations enrolled in Part A of this study will be continuously monitored.

Part A1 will evaluate the safety, tolerability, PK, and pharmacodynamics (PD) of compound 1 in participants with BRAF mutation-positive advanced or metastatic solid tumors and/or melanoma harboring an NRAS mutation. This component will combine an accelerated titration design (single participant dose levels) followed by a traditional 3+3 dose escalation schema to identify the MTD and/or RP2D of compound 1. The MTD is defined as the maximum daily oral dose at which <33% of participants experience a DLT during the 28-day DLT evaluation period. Compound 1 will be administered as an oral dose twice daily (BID) every day for 28 days in 28-day treatment cycles.

The starting dose, Dose Level 1 (DL1), will be 50 mg per day (administered as 25 mg BID), and dose escalation increments will follow a modified Fibonacci sequence. The planned compound 1 dose levels are indicated in the protocol.

An accelerated titration dose escalation design principle will be employed in which 1 participant per cohort will be evaluated until evidence of biologic activity is observed, at which time that cohort will be expanded by 2 participants. This and all subsequent dose level cohorts will proceed using the 3+3 dose escalation design. For purposes of the above discussion, "evidence of biologic activity" is defined as either (1) a DLT or (2) at least 1 Grade≥2 adverse event (AE) not clearly attributable to underlying disease or extraneous cause (excluding Grade 2 Laboratory Investigation AEs deemed non-clinically significant by the Investigator).

Starting with DL3, the compound 1 dose will be escalated using a traditional 3+3 study design and will continue until stopping rules are met, or until the MTD or the dose at which the anticipated maximal pharmacologic activity (informed by PK and PD biomarkers) is achieved. With this 3+3 design, at least 3 participants will be enrolled into each dose level from DL3 onwards. If none of the 3 participants in a dose level experiences a DLT within the DLT period (28 days from the first dose of compound 1 for all dose levels), another 3 participants will be treated at the next higher dose level. No additional participants will be treated at a given dose level if 2 or more of the participants in that dose level develop a DLT in Cycle 1.

For the first 2 participants who receive compound 1 at a specified dose level, there will be at least 24 hours between the first dose of compound 1 in the first and second participants.

Dose escalation will continue until the highest planned dose level is determined to be safe and tolerable with a minimum of 6 DLT-evaluable participants at that dose level (i.e., the dose level considered to be the RP2D), or until MTD is reached. Up to approximately 26 participants will be required to estimate the MTD and/or the RP2D.

The Dose Review Committee (DRC) consisting of Investigators and Sponsor representatives will review all available safety, PK, and PD data prior to initiating enrollment at the next dose level. The DRC will review the safety and tolerability of each dose level of compound 1 monotherapy after participants at that particular dose level have completed at least 1 full cycle. Part A will continue until stopping rules are met or until the MTD or the dose where the anticipated maximal pharmacologic activity (e.g., RP2D) is achieved. The DRC will also evaluate all available safety data and PK/PD data to determine the RP2D for Part B.

Should a participant who is receiving compound 1 monotherapy experience disease progression while on treatment, the participant may be given the option to receive the combination of compound 1+binimetinib, based on the participant's eligibility for the combination treatment, experience with compound 1 therapy, characteristics of response, or other relevant considerations. This decision is at the Investigator's discretion but should be made in consultation with the Sponsor.

Part A2 will not be initiated until preliminary proof of mechanism (PPOM) clinical criteria have been met in the monotherapy dose escalation cohorts. Eligibility will be limited to participants with Class II/III BRAF and/or NRAS mutated tumors. A parallel escalation will be initiated with compound 1 and binimetinib (binimetinib at a dose of 45 mg orally [PO] BID). The starting dose of compound 1 in combination (designated combination dose level 1) will be 1 dose level below that at which the PPOM criteria have been met or 1 dose level below the highest dose level considered safe, at the discretion of the DRC. The dose escalation will follow a 3+3 design as described in the protocol. compound 1 and binimetinib will be administered together as an oral dose BID every day in 28-day treatment cycles in participants with Class II/III BRAF and NRAS mutated tumors.

At the end of each dosing cohort, the DRC will be responsible for determining whether the criteria for PPOM have been met, and for recommending if the combination dose escalation should be initiated. Once the combination dose escalation has initiated, specific compound 1 doses will increase according to modified Fibonacci design and intermediate doses may be selected in practice.

Intra-participant dose escalations and backfill are allowed in Part A1 at the discretion of the Investigator and after consultation with the Sponsor. Intra-participant dose escalation may only be considered if the participant meets all of the protocol-specified criteria.

The effect of food on the PK of compound 1 will be evaluated in at least 6 participants during Part A1 in participants at DL3, DL4, and DL5 using a randomized crossover design.

Part B (Dose Expansion)

The dose expansion part of the study (Part B) can begin once the MTD and/or a biologically active dose (i.e., RP2D]) has been determined in Part A from the compound 1 monotherapy group. Part B will evaluate the antitumor activity of compound 1 at the RP2D determined from Part A in the following cohorts:

- Cohort 1: Participants with unresectable and locally advanced (American Joint Committee on Cancer [AJCC] Stage III) or metastatic (AJCC Stage IV) non-small-cell lung cancer (NSCLC) with any BRAF Class II or Class III mutation
- Cohort 2: Participants with unresectable and locally advanced (AJCC Stage III) or metastatic (AJCC Stage IV) melanoma with any BRAF Class II or Class III mutation
- Cohort 3: Participants with any unresectable and locally advanced (AJCC Stage III, or comparable Stage with other staging systems) or metastatic (AJCC Stage IV) solid tumor (other than NSCLC or melanoma) with any BRAF Class II or Class III mutation Enrollment of participants in the Dose Expansion cohorts will occur concurrently.

In Cohort 3, enrollment of participants with various tumor types harboring BRAF Class II or Class III mutations will be monitored during the course of this study; enrollment of specific tumor types may be restricted to ensure broad representation of various solid tumors in this cohort.

Study Endpoints

Primary

Safety endpoints include the following:

- Incidence of DLTs,
- Incidence of AEs, including treatment-emergent adverse events and treatment-related AEs
- Clinically significant changes in vital signs, physical examinations, electrocardiograms, and clinical laboratory tests Efficacy (as assessed by the Investigator) will be measured by the following:

- Objective response rate, defined as the rate of partial responses plus complete responses according to Response Evaluation Criteria in Solid Tumors (RECIST) v1.1 as assessed by the Investigator.
- Disease control rate
- Duration of overall response
- Duration of stable disease

Secondary

- Pharmacokinetic parameters of compound 1 and compound 1+binimetinib including, but not limited to, maximum observed plasma concentration (Cmax), time to achieve Cmax (tmax), and area under the plasma concentration-time curve (AUC), including in the fed and fasted states.

Exploratory

- Compound 1 and compound 1+binimetinib exposure/safety and exposure/efficacy relationships
- Characterization of potential metabolites of compound 1 in plasma and urine
- Progression-free survival, and overall survival
- Biomarker quantification by biochemical and/or genetic analysis of blood and/or tumor samples including, but not limited to, the pharmacodynamic effect on phosphoextracellular signal-regulated kinase (ERK), DUSP6 ribonucleic acid (RNA) and proliferation marker, Ki-67.
- Changes in circulating tumor-derived (blood) nucleic acids (ctDNA) concentration and mutational profiles
- Potential biomarkers by biochemical and/or genetic analysis of blood and/or tumor samples
- Population PK analysis

Sample Size

Approximately 155 participants are planned be enrolled in this study.

Part A (Dose Escalation)

In Part A1, up to 41 participants will be enrolled in the monotherapy dose escalation phase. Approximately 26 participants may be enrolled to estimate the MTD and/or RP2D from which 6 participants will be evaluated for food effect on the PK of compound 1.

For Part A2, up to 36 participants will be enrolled in the combination dose escalation phase. Approximately 24 participants may be needed to estimate the MTD of the compound 1+binimetinib combination.

Approximately 30 additional participants may be enrolled for backfill across Parts A1 and A2.

Part B (Dose Expansion)

Approximately 75 participants will be enrolled in Part B, which will include 3 cohorts of participants with BRAF Class II or III mutations, including participants with NSCLC, melanoma, and other solid tumors. For Cohorts 1 and 2, a Simon's 2-stage optimal design is planned. Twelve participants will be enrolled in the first stage. If ≥3 participants respond, it will proceed to stage 2 enrolling additional 13 participants for a total sample size of 25 in the cohort. At the end of stage 2, if ≥8 of the 25 participants respond, compound 1 will be considered promising for further evaluation. Within each cohort, the design has 80% power and a maximum type-1 error rate of 0.1 to test the null hypothesis that the response rate is ≤20% against the alternative hypothesis of ≥40%. For the futility assessment in stage 1, response may not require confirmation. Additional considerations beyond the response rate may also be included at the discretion of the DRC and Sponsor.

Key Inclusion and Exclusion Criteria

Key inclusion criteria include the following:

Adult participants (≥18 years of age) with histologically or cytologically confirmed diagnosis of metastatic or advanced-stage malignancy will be eligible for this study. Part A, dose escalation, will enroll participants with any type of advanced or metastatic solid tumor. Part B, dose expansion, will enroll participants with unresectable and locally advanced (AJCC Stage III) or metastatic (AJCC Stage IV) NSCLC, unresectable and locally advanced (AJCC Stage III) or metastatic (AJCC Stage IV) melanoma, or any unresectable and locally advanced (AJCC Stage III, or comparable Stage with other staging systems) or metastatic (AJCC Stage IV) solid tumor other than NSCLC or melanoma. Additionally, genetic abnormalities of BRAF and/or NRAS are required as specified in the inclusion criteria. Participants must have received prior standard therapy appropriate for their tumor type and stage of disease, or in the opinion of the Investigator, would be unlikely to tolerate or derive clinically meaningful benefit from appropriate standard of care therapy. In Part A1, participants with specific cancers (NSCLC, melanoma, colorectal cancer [CRC] and anaplastic thyroid cancer) driven by BRAF Class I mutations, should have previously received an approved BRAF inhibitor (with or without an approved MEK inhibitor, if authorized and available).

The participant's tumor must harbor a BRAF mutation or be melanoma with an NRAS mutation identified by previous genomic analysis of tumor tissue or ctDNA conducted in a Clinical Laboratory Improvement Amendments (CLIA)-certified laboratory (in United States [US]) or in accordance with local regulatory requirements (in other countries). Participants will provide archived tumor tissue specimen (formalin-fixed paraffin-embedded [FFPE] specimen) obtained within the last 5 years (if available), and will undergo mandatory pre-treatment tumor biopsy, if medically feasible. A complete list of inclusion/exclusion criteria is included in the protocol.

Key exclusion criteria include the following:

Participants with known active brain metastases from non-brain tumors are not eligible. Participants in Part A with other solid tumors (other than NSCLC, melanoma, CRC, and anaplastic thyroid cancer) driven by BRAF Class I mutation may not have had prior treatment with any approved or in-development small molecule BRAF-, MEK-, or mitogen activated protein kinase (MAPK)-directed inhibitor therapy. This criterion will not be implemented until a decision to do so is made and communicated by the DRC. In Part B, previous treatment with any approved or in-development small molecule BRAF-, MEK-, or MAPK-directed inhibitor therapy is excluded. Participants may not have any unresolved toxicities from prior anti-tumor therapy. Participants may not have any unresolved toxicities from prior anti-tumor therapy. Exclusionary concomitant medications, contraception requirements, and diseases and other conditions which would exclude a participant from the study are detailed in the protocol.

Treatment Duration Participants will receive compound 1 or compound 1+binimetinib in 28-day cycles until evidence of disease progression, unacceptable toxicity, intolerance to study medication, initiation of new systemic therapy for cancer, withdrawal of consent, Investigator decision, Sponsor decision, or death.

Statistical Considerations Descriptive statistics will be provided for selected demographics, safety, PK, efficacy and biomarker data by dose, dose schedule, and time as appropriate. Descriptive statistics on continuous data will include means, medians, standard deviations, and ranges, while categorical data will be summarized using frequency counts and percentages. Objective response rate will be presented with 95% exact confidence interval. Graphical summaries of the data may also be presented.

What is claimed is:

1. A method of treating a cancer in a patient in need thereof, comprising administering to the patient (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof.

2. The method of claim 1, wherein the cancer is characterized as having an oncogenic BRAF alteration.

3. The method of claim 2, wherein the oncogenic BRAF alteration is a BRAF V600 mutation.

4. The method of claim 3, wherein the BRAF V600 mutation is a V600E or V600K mutation.

5. The method of claim 1, wherein the cancer is characterized as having a wild type BRAF.

6. The method of claim 1, wherein the cancer is a solid tumor.

7. The method of claim 1, wherein the cancer is selected from melanoma, pancreatic cancer, pancreatic adenocarcinoma, ovarian cancer, colorectal cancer, glioma, Langerhans cell histiocytosis, leukemia, hairy cell leukemia, thyroid cancer, anaplastic thyroid cancer, papillary thyroid carcinoma, follicular thyroid carcinoma, or medullary thyroid carcinoma.

8. The method of claim 1, wherein the cancer is selected from small cell lung cancer, non-small cell lung cancer, prostate cancer, gastric cancer, esophageal cancer, NRAS mutant melanoma, or colorectal cancer.

9. The method of claim 1, wherein the cancer is metastatic.

10. The method of claim 1, wherein the method is adjuvant therapy following surgical resection.

11. The method of claim 1, wherein the patient has relapsed after prior therapy, has acquired resistance to prior therapy, or is refractory to therapy.

12. The method of claim 1, wherein the (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, is administered orally.

13. A method of treating a cancer in a patient in need thereof, comprising administering to the patient a pharmaceutical composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof, and at least one pharmaceutically acceptable excipient.

14. A method of treating a cancer in a patient in need thereof, comprising administering to the patient:

(a) a composition comprising (S)—N-(3-(2-(((R)-1-hydroxypropan-2-yl)amino)-6-morpholinopyridin-4-yl)-4-methylphenyl)-3-(2,2,2-trifluoroethyl)pyrrolidine-1-carboxamide, or pharmaceutically acceptable salt or solvate thereof; and (b) at least one oncology therapeutic selected from a MEK inhibitor, an immune checkpoint inhibitor, a CDK inhibitor, an EGFR kinase inhibitor, an EGFR antibody, an EGFR PROTAC therapeutic, a FGFR inhibitor, a SOS1 inhibitor, a SHP2 inhibitor, a KRAS inhibitor, a taxane, a topoisomerase inhibitor, an ERK inhibitor, a platinum-based chemotherapy, folinic acid, 5-fluorouracil, or an anti-VEGF therapeutic.

15. The method of claim 14, wherein the immune checkpoint inhibitor is a CTLA-4 inhibitor, a PD-1 inhibitor, or a PD-L1 inhibitor, and the CDK inhibitor is a CDK4/6 inhibitor.

16. The method of claim 14, wherein the MEK inhibitor is selected from binimetinib, trametinib, cobimetinib, selumetinib, pimasertib, or mirdametinib; the CTLA-4 inhibitor is ipilimumab; the PD-1 inhibitor is spartalizumab, nivolumab, pembrolizumab, or cemiplimab; the PD-L1 inhibitor is atezolizumab, avelumab, or durvalumab; the CDK4/6 inhibitor is palbociclib, abemaciclib, or ribociclib; the EGFR kinase inhibitor is nazartinib, gefitinib, erlotinib, afatinib, brigatinib, icotinib, neratinib, osimertinib, dacomitinib, or lapatinib; the EGFR antibody is cetuximab, panitumumab, zalutumumab, nimotuzumab, or matuzumab; the KRAS inhibitor is sotorasib, adagrasib, or BI-1701963; the topoisomerase inhibitor is irinotecan, topotecan, or belotecan; the platinum-based chemotherapy is oxaliplatin, cisplatin, or carboplatin; and the anti-VEGF therapeutic is bevacizumab or aflibercept.

17. The method of claim 14, wherein the at least one oncology therapeutic is a MEK inhibitor.

18. The method of claim 17, wherein the MEK inhibitor is selected from binimetinib, trametinib, cobimetinib, selumetinib, pimasertib, or mirdametinib.

19. The method of claim 18, wherein the MEK inhibitor is binimetinib.

20. The method of claim 14, wherein the at least one oncology therapeutic is an EGFR antibody.

21. The method of claim 20, wherein the EGFR antibody is cetuximab, panitumumab, zalutumumab, nimotuzumab, or matuzumab.

22. The method of claim 21, wherein the EGFR antibody is cetuximab.

23. The method of claim 14, wherein the cancer is characterized as having an oncogenic BRAF alteration.

24. The method of claim 23, wherein the oncogenic BRAF alteration is a BRAF V600 mutation.

25. The method of claim 24, wherein the BRAF V600 mutation is a V600E or V600K mutation.

26. The method of claim 14, wherein the cancer is characterized as having a wild type BRAF.

27. The method of claim 14, wherein the cancer is a solid tumor.

28. The method of claim 14, wherein the cancer is selected from melanoma, pancreatic cancer, pancreatic adenocarcinoma, ovarian cancer, colorectal cancer, glioma, Langerhans cell histiocytosis, leukemia, hairy cell leukemia, thyroid cancer, anaplastic thyroid cancer, papillary thyroid carcinoma, follicular thyroid carcinoma, or medullary thyroid carcinoma.

29. The method of claim 14, wherein the cancer is selected from small cell lung cancer, non-small cell lung cancer, prostate cancer, gastric cancer, esophageal cancer, NRAS mutant melanoma or colorectal cancer.

30. The method of claim 14, wherein the cancer is metastatic.

31. The method of claim 14, wherein the method is adjuvant therapy following surgical resection.

* * * * *